(12) United States Patent
Tomatsu et al.

(10) Patent No.: US 8,226,940 B2
(45) Date of Patent: Jul. 24, 2012

(54) ENHANCING THE EFFECT OF THERAPEUTIC PROTEINS ON THE CENTRAL NERVOUS SYSTEM

(75) Inventors: Shunji Tomatsu, Wilmington, DE (US); Adriana Montano, St. Louis, MO (US); Tatsuo Nishioka, Ishikawa (JP); Jeffrey H. Grubb, St. Louis, MO (US); William S. Sly, St. Louis, MO (US); Monica A. Gutierrez, Cucuta Norte de Santander (CO); Amelia Ortigoza Rodriguez, legal representative, Cucuta Norte de Santander (CO)

(73) Assignee: Saint Louis University, Saint Louis, MO (US)

(*) Notice: Subject to any disclaimer, the term of this patent is extended or adjusted under 35 U.S.C. 154(b) by 131 days.

(21) Appl. No.: 12/714,534

(22) Filed: Feb. 28, 2010

(65) Prior Publication Data

US 2010/0158889 A1  Jun. 24, 2010

Related U.S. Application Data

(60) Division of application No. 11/614,970, filed on Dec. 21, 2006, now abandoned, which is a continuation-in-part of application No. 11/245,424, filed on Oct. 7, 2005, now abandoned, which is a continuation-in-part of application No. 10/864,758, filed on Jun. 10, 2004, now Pat. No. 7,863,238.

(51) Int. Cl.
*A61K 38/47* (2006.01)
*A61K 38/43* (2006.01)
*A61K 38/00* (2006.01)
*C12N 9/24* (2006.01)
*C12N 9/14* (2006.01)
*C07H 21/04* (2006.01)
*C07K 1/00* (2006.01)

(52) U.S. Cl. ............ 424/94.61; 424/94.1; 514/1.1; 514/18.1; 435/200; 435/195; 536/23.2; 530/350

(58) Field of Classification Search ........... 424/94.61, 424/94.1; 514/1.1, 18.1; 435/200, 195; 536/23.2; 530/350
See application file for complete search history.

(56) References Cited

U.S. PATENT DOCUMENTS

2002/0169125 A1 * 11/2002 Leung et al. .............. 514/12

FOREIGN PATENT DOCUMENTS

WO  WO 99/33957  *  7/1999

OTHER PUBLICATIONS

Urayama et al. Developmentally regulated mannose 6-phosphate receptor-mediated transport of a lysosomal enzyme across the blood-brain barrier. PNAS., 2004, vol. 101 (34): 12658-12663.*

* cited by examiner

*Primary Examiner* — Ganapathirama Raghu
(74) *Attorney, Agent, or Firm* — Randolph Bretton; The Law Office of Randolph Bretton

(57) ABSTRACT

The present invention provides a polypeptide therapeutic agent, useful in enzyme replacement therapy, with increased therapeutic benefits for the central nervous system. The invention provides a method of enhancing the effect of a polypeptide or protein on the central nervous system by the attachment of a short acidic amino acid sequence. Specifically the inventors disclose the attachment of a 4-15 acidic amino acid sequence to human β-glucuronidase by construction of a fusion protein. This molecule is useful in the treatment of type VII mucopolysaccharidosis when administered to a patient.

14 Claims, 4 Drawing Sheets

CLEALANCE of NATIVE and NBT-GUSs

Neocortex

GUS Treatment        D6 BT GUS

SEQUENCE LISTING

<160> NUMBER OF SEQ ID NOS: 19

<210> SEQ ID NO 1
<211> LENGTH: 1956
<212> TYPE: DNA
<213> ORGANISM: Homo sapiens
<220> FEATURE:
<221> NAME/KEY: SIG_PEPTIDE
<222> LOCATION: (1)..(66)
<220> FEATURE:
<221> NAME/KEY: CDS
<222> LOCATION: (67)..(1953)
<223> OTHER INFORMATION: CODING REGION FOR MATURE GUS

<400> SEQUENCE: 1

```
atggcccggg ggtcggcggt tgcctgggcg gcgctcgggc cgttgttgtg gggctgcgcg      60 ctgggg ctg cag ggc ggg atg ctg tac ccc cag gag agc ccg tcg cgg       108
       Leu Gln Gly Gly Met Leu Tyr Pro Gln Glu Ser Pro Ser Arg
       1               5                   10 gag tgc aag gag ctg gac ggc ctc tgg agc ttc cgc gcc gac ttc tct       156
Glu Cys Lys Glu Leu Asp Gly Leu Trp Ser Phe Arg Ala Asp Phe Ser
15                  20                  25                  30 gac aac cga cgc cgg ggc ttc gag gag cag tgg tac cgg cgg ccg ctg       204
Asp Asn Arg Arg Arg Gly Phe Glu Glu Gln Trp Tyr Arg Arg Pro Leu
                35                  40                  45 tgg gag tca ggc ccc acc gtg gac atg cca gtt ccc tcc agc ttc aat       252
Trp Glu Ser Gly Pro Thr Val Asp Met Pro Val Pro Ser Ser Phe Asn
            50                  55                  60 gac atc agc cag gac tgg cgt ctg cgg cat ttt gtc ggc tgg gtg tgg       300
Asp Ile Ser Gln Asp Trp Arg Leu Arg His Phe Val Gly Trp Val Trp
        65                  70                  75 tac gaa cgg gag gtg atc ctg ccg gag cga tgg acc cag gac ctg cgc       348
Tyr Glu Arg Glu Val Ile Leu Pro Glu Arg Trp Thr Gln Asp Leu Arg
    80                  85                  90 aca aga gtg gtg ctg agg att ggc agt gcc cat tcc tat gcc atc gtg       396
Thr Arg Val Val Leu Arg Ile Gly Ser Ala His Ser Tyr Ala Ile Val
95                  100                 105                 110 tgg gtg aat ggg gtc gac acg cta gag cat gag ggg ggc tac ctc ccc       444
Trp Val Asn Gly Val Asp Thr Leu Glu His Glu Gly Gly Tyr Leu Pro
                115                 120                 125 ttc gag gcc gac atc agc aac ctg gtc cag gtg ggg ccc ctg ccc tcc       492
Phe Glu Ala Asp Ile Ser Asn Leu Val Gln Val Gly Pro Leu Pro Ser
            130                 135                 140 cgg ctc cga atc act atc gcc atc aac aac aca ctc acc ccc acc acc       540
Arg Leu Arg Ile Thr Ile Ala Ile Asn Asn Thr Leu Thr Pro Thr Thr
        145                 150                 155 ctg cca cca ggg acc atc caa tac ctg act gac acc tcc aag tat ccc       588
Leu Pro Pro Gly Thr Ile Gln Tyr Leu Thr Asp Thr Ser Lys Tyr Pro
    160                 165                 170 aag ggt tac ttt gtc cag aac aca tat ttt gac ttt ttc aac tac gct       636
Lys Gly Tyr Phe Val Gln Asn Thr Tyr Phe Asp Phe Phe Asn Tyr Ala
175                 180                 185                 190 gga ctg cag cgg tct gta ctt ctg tac acg aca ccc acc acc tac atc       684
Gly Leu Gln Arg Ser Val Leu Leu Tyr Thr Thr Pro Thr Thr Tyr Ile
                195                 200                 205 gat gac atc acc gtc acc acc agc gtg gag caa gac agt ggg ctg gtg       732
Asp Asp Ile Thr Val Thr Thr Ser Val Glu Gln Asp Ser Gly Leu Val
            210                 215                 220 aat tac cag atc tct gtc aag ggc agt aac ctg ttc aag ttg gaa gtg       780
Asn Tyr Gln Ile Ser Val Lys Gly Ser Asn Leu Phe Lys Leu Glu Val
        225                 230                 235
```

|     |     |     |     |     |     |     |     |     |     |     |     |     |     |     |     |      |
|-----|-----|-----|-----|-----|-----|-----|-----|-----|-----|-----|-----|-----|-----|-----|-----|------|
| cgt | ctt | ttg | gat | gca | gaa | aac | aaa | gtc | gtg | gcg | aat | ggg | act | ggg | acc | 828  |
| Arg | Leu | Leu | Asp | Ala | Glu | Asn | Lys | Val | Val | Ala | Asn | Gly | Thr | Gly | Thr |      |
|     | 240 |     |     |     | 245 |     |     |     |     | 250 |     |     |     |     |     |      |
| cag | ggc | caa | ctt | aag | gtg | cca | ggt | gtc | agc | ctc | tgg | tgg | ccg | tac | ctg | 876  |
| Gln | Gly | Gln | Leu | Lys | Val | Pro | Gly | Val | Ser | Leu | Trp | Trp | Pro | Tyr | Leu |      |
| 255 |     |     |     |     | 260 |     |     |     |     | 265 |     |     |     |     | 270 |      |
| atg | cac | gaa | cgc | cct | gcc | tat | ctg | tat | tca | ttg | gag | gtg | cag | ctg | act | 924  |
| Met | His | Glu | Arg | Pro | Ala | Tyr | Leu | Tyr | Ser | Leu | Glu | Val | Gln | Leu | Thr |      |
|     |     |     | 275 |     |     |     |     | 280 |     |     |     |     | 285 |     |     |      |
| gca | cag | acg | tca | ctg | ggg | cct | gtg | tct | gac | ttc | tac | aca | ctc | cct | gtg | 972  |
| Ala | Gln | Thr | Ser | Leu | Gly | Pro | Val | Ser | Asp | Phe | Tyr | Thr | Leu | Pro | Val |      |
|     |     |     | 290 |     |     |     |     | 295 |     |     |     |     | 300 |     |     |      |
| ggg | atc | cgc | act | gtg | gct | gtc | acc | aag | agc | cag | ttc | ctc | atc | aat | ggg | 1020 |
| Gly | Ile | Arg | Thr | Val | Ala | Val | Thr | Lys | Ser | Gln | Phe | Leu | Ile | Asn | Gly |      |
|     |     | 305 |     |     |     |     | 310 |     |     |     |     | 315 |     |     |     |      |
| aaa | cct | ttc | tat | ttc | cac | ggt | atc | aca | aag | cat | gag | gat | gcg | gac | atc | 1068 |
| Lys | Pro | Phe | Tyr | Phe | His | Gly | Ile | Thr | Lys | His | Glu | Asp | Ala | Asp | Ile |      |
| 320 |     |     |     |     | 325 |     |     |     |     | 330 |     |     |     |     |     |      |
| cga | ggg | aag | ggc | ttc | gac | tgg | ccg | ctg | ctg | gtg | aag | gac | ttc | aac | ctg | 1116 |
| Arg | Gly | Lys | Gly | Phe | Asp | Trp | Pro | Leu | Leu | Val | Lys | Asp | Phe | Asn | Leu |      |
| 335 |     |     |     | 340 |     |     |     |     | 345 |     |     |     |     | 350 |     |      |
| ctt | cgc | tgg | ctt | ggt | gcc | aac | gct | ttc | cgt | acc | agc | cac | tac | ccc | tat | 1164 |
| Leu | Arg | Trp | Leu | Gly | Ala | Asn | Ala | Phe | Arg | Thr | Ser | His | Tyr | Pro | Tyr |      |
|     |     |     | 355 |     |     |     |     | 360 |     |     |     |     | 365 |     |     |      |
| gca | gag | gaa | gtg | atg | cag | atg | tgt | gac | cgc | tat | ggg | att | gtg | gtc | atc | 1212 |
| Ala | Glu | Glu | Val | Met | Gln | Met | Cys | Asp | Arg | Tyr | Gly | Ile | Val | Val | Ile |      |
|     |     |     | 370 |     |     |     |     | 375 |     |     |     |     | 380 |     |     |      |
| gat | gag | tgt | ccc | ggc | gtg | ggc | ctg | gcg | ctg | ccg | cag | ttc | ttc | aac | aac | 1260 |
| Asp | Glu | Cys | Pro | Gly | Val | Gly | Leu | Ala | Leu | Pro | Gln | Phe | Phe | Asn | Asn |      |
|     |     | 385 |     |     |     |     | 390 |     |     |     |     | 395 |     |     |     |      |
| gtt | tct | ctg | cat | cac | cac | atg | cag | gtg | atg | gaa | gaa | gtg | gtg | cgt | agg | 1308 |
| Val | Ser | Leu | His | His | His | Met | Gln | Val | Met | Glu | Glu | Val | Val | Arg | Arg |      |
|     | 400 |     |     |     |     | 405 |     |     |     |     | 410 |     |     |     |     |      |
| gac | aag | aac | cac | ccc | gcg | gtc | gtg | atg | tgg | tct | gtg | gcc | aac | gag | cct | 1356 |
| Asp | Lys | Asn | His | Pro | Ala | Val | Val | Met | Trp | Ser | Val | Ala | Asn | Glu | Pro |      |
| 415 |     |     |     |     | 420 |     |     |     |     | 425 |     |     |     |     | 430 |      |
| gcg | tcc | cac | cta | gaa | tct | gct | ggc | tac | tac | ttg | aag | atg | gtg | atc | gct | 1404 |
| Ala | Ser | His | Leu | Glu | Ser | Ala | Gly | Tyr | Tyr | Leu | Lys | Met | Val | Ile | Ala |      |
|     |     |     |     | 435 |     |     |     |     | 440 |     |     |     |     | 445 |     |      |
| cac | acc | aaa | tcc | ttg | gac | ccc | tcc | cgg | cct | gtg | acc | ttt | gtg | agc | aac | 1452 |
| His | Thr | Lys | Ser | Leu | Asp | Pro | Ser | Arg | Pro | Val | Thr | Phe | Val | Ser | Asn |      |
|     |     |     | 450 |     |     |     |     | 455 |     |     |     |     | 460 |     |     |      |
| tct | aac | tat | gca | gca | gac | aag | ggg | gct | ccg | tat | gtg | gat | gtg | atc | tgt | 1500 |
| Ser | Asn | Tyr | Ala | Ala | Asp | Lys | Gly | Ala | Pro | Tyr | Val | Asp | Val | Ile | Cys |      |
|     |     | 465 |     |     |     |     | 470 |     |     |     |     | 475 |     |     |     |      |
| ttg | aac | agc | tac | tac | tct | tgg | tat | cac | gac | tac | ggg | cac | ctg | gag | ttg | 1548 |
| Leu | Asn | Ser | Tyr | Tyr | Ser | Trp | Tyr | His | Asp | Tyr | Gly | His | Leu | Glu | Leu |      |
|     | 480 |     |     |     |     | 485 |     |     |     |     | 490 |     |     |     |     |      |
| att | cag | ctg | cag | ctg | gcc | acc | cag | ttt | gag | aac | tgg | tat | aag | aag | tat | 1596 |
| Ile | Gln | Leu | Gln | Leu | Ala | Thr | Gln | Phe | Glu | Asn | Trp | Tyr | Lys | Lys | Tyr |      |
| 495 |     |     |     | 500 |     |     |     |     | 505 |     |     |     |     | 510 |     |      |
| cag | aag | ccc | att | att | cag | agc | gag | tat | gga | gca | gaa | acg | att | gca | ggg | 1644 |
| Gln | Lys | Pro | Ile | Ile | Gln | Ser | Glu | Tyr | Gly | Ala | Glu | Thr | Ile | Ala | Gly |      |
|     |     |     |     | 515 |     |     |     |     | 520 |     |     |     |     | 525 |     |      |
| ttt | cac | cag | gat | cca | cct | ctg | atg | ttc | act | gaa | gag | tac | cag | aaa | agt | 1692 |
| Phe | His | Gln | Asp | Pro | Pro | Leu | Met | Phe | Thr | Glu | Glu | Tyr | Gln | Lys | Ser |      |
|     |     |     | 530 |     |     |     |     | 535 |     |     |     |     | 540 |     |     |      |
| ctg | cta | gag | cag | tac | cat | ctg | ggt | ctg | gat | caa | aaa | cgc | aga | aaa | tac | 1740 |
| Leu | Leu | Glu | Gln | Tyr | His | Leu | Gly | Leu | Asp | Gln | Lys | Arg | Arg | Lys | Tyr |      |
|     | 545 |     |     |     |     | 550 |     |     |     |     | 555 |     |     |     |     |      |

```
gtg gtt gga gag ctc att tgg aat ttt gcc gat ttc atg act gaa cag    1788
Val Val Gly Glu Leu Ile Trp Asn Phe Ala Asp Phe Met Thr Glu Gln
    560                 565                 570 tca ccg acg aga gtg ctg ggg aat aaa aag ggg atc ttc act cgg cag    1836
Ser Pro Thr Arg Val Leu Gly Asn Lys Lys Gly Ile Phe Thr Arg Gln
575                 580                 585                 590 aga caa cca aaa agt gca gcg ttc ctt ttg cga gag aga tac tgg aag    1884
Arg Gln Pro Lys Ser Ala Ala Phe Leu Leu Arg Glu Arg Tyr Trp Lys
                595                 600                 605 att gcc aat gaa acc agg tat ccc cac tca gta gcc aag tca caa tgt    1932
Ile Ala Asn Glu Thr Arg Tyr Pro His Ser Val Ala Lys Ser Gln Cys
            610                 615                 620 ttg gaa aac agc ctg ttt act tga                                    1956
Leu Glu Asn Ser Leu Phe Thr
        625

<210> SEQ ID NO 2
<211> LENGTH: 629
<212> TYPE: PRT
<213> ORGANISM: Homo sapiens

<400> SEQUENCE: 2

Leu Gln Gly Gly Met Leu Tyr Pro Gln Glu Ser Pro Ser Arg Glu Cys
1               5                   10                  15

Lys Glu Leu Asp Gly Leu Trp Ser Phe Arg Ala Asp Phe Ser Asp Asn
            20                  25                  30

Arg Arg Arg Gly Phe Glu Glu Gln Trp Tyr Arg Arg Pro Leu Trp Glu
        35                  40                  45

Ser Gly Pro Thr Val Asp Met Pro Val Pro Ser Ser Phe Asn Asp Ile
50                  55                  60

Ser Gln Asp Trp Arg Leu Arg His Phe Val Gly Trp Val Trp Tyr Glu
65                  70                  75                  80

Arg Glu Val Ile Leu Pro Glu Arg Trp Thr Gln Asp Leu Arg Thr Arg
                85                  90                  95

Val Val Leu Arg Ile Gly Ser Ala His Ser Tyr Ala Ile Val Trp Val
            100                 105                 110

Asn Gly Val Asp Thr Leu Glu His Glu Gly Gly Tyr Leu Pro Phe Glu
        115                 120                 125

Ala Asp Ile Ser Asn Leu Val Gln Val Gly Pro Leu Pro Ser Arg Leu
130                 135                 140

Arg Ile Thr Ile Ala Ile Asn Asn Thr Leu Thr Pro Thr Thr Leu Pro
145                 150                 155                 160

Pro Gly Thr Ile Gln Tyr Leu Thr Asp Thr Ser Lys Tyr Pro Lys Gly
                165                 170                 175

Tyr Phe Val Gln Asn Thr Tyr Phe Asp Phe Phe Asn Tyr Ala Gly Leu
            180                 185                 190

Gln Arg Ser Val Leu Leu Tyr Thr Thr Pro Thr Thr Tyr Ile Asp Asp
        195                 200                 205

Ile Thr Val Thr Thr Ser Val Glu Gln Asp Ser Gly Leu Val Asn Tyr
210                 215                 220

Gln Ile Ser Val Lys Gly Ser Asn Leu Phe Lys Leu Glu Val Arg Leu
225                 230                 235                 240

Leu Asp Ala Glu Asn Lys Val Val Ala Asn Gly Thr Gly Thr Gln Gly
                245                 250                 255

Gln Leu Lys Val Pro Gly Val Ser Leu Trp Trp Pro Tyr Leu Met His
            260                 265                 270
```

-continued

Glu Arg Pro Ala Tyr Leu Tyr Ser Leu Glu Val Gln Leu Thr Ala Gln
275                 280                 285

Thr Ser Leu Gly Pro Val Ser Asp Phe Tyr Thr Leu Pro Val Gly Ile
290                 295                 300

Arg Thr Val Ala Val Thr Lys Ser Gln Phe Leu Ile Asn Gly Lys Pro
305                 310                 315                 320

Phe Tyr Phe His Gly Ile Thr Lys His Glu Asp Ala Asp Ile Arg Gly
                325                 330                 335

Lys Gly Phe Asp Trp Pro Leu Leu Val Lys Asp Phe Asn Leu Leu Arg
                340                 345                 350

Trp Leu Gly Ala Asn Ala Phe Arg Thr Ser His Tyr Pro Tyr Ala Glu
                355                 360                 365

Glu Val Met Gln Met Cys Asp Arg Tyr Gly Ile Val Val Ile Asp Glu
370                 375                 380

Cys Pro Gly Val Gly Leu Ala Leu Pro Gln Phe Phe Asn Asn Val Ser
385                 390                 395                 400

Leu His His His Met Gln Val Met Glu Glu Val Val Arg Arg Asp Lys
                405                 410                 415

Asn His Pro Ala Val Val Met Trp Ser Val Ala Asn Glu Pro Ala Ser
                420                 425                 430

His Leu Glu Ser Ala Gly Tyr Tyr Leu Lys Met Val Ile Ala His Thr
                435                 440                 445

Lys Ser Leu Asp Pro Ser Arg Pro Val Thr Phe Val Ser Asn Ser Asn
450                 455                 460

Tyr Ala Ala Asp Lys Gly Ala Pro Tyr Val Asp Val Ile Cys Leu Asn
465                 470                 475                 480

Ser Tyr Tyr Ser Trp Tyr His Asp Tyr Gly His Leu Glu Leu Ile Gln
                485                 490                 495

Leu Gln Leu Ala Thr Gln Phe Glu Asn Trp Tyr Lys Lys Tyr Gln Lys
                500                 505                 510

Pro Ile Ile Gln Ser Glu Tyr Gly Ala Glu Thr Ile Ala Gly Phe His
                515                 520                 525

Gln Asp Pro Pro Leu Met Phe Thr Glu Glu Tyr Gln Lys Ser Leu Leu
530                 535                 540

Glu Gln Tyr His Leu Gly Leu Asp Gln Lys Arg Arg Lys Tyr Val Val
545                 550                 555                 560

Gly Glu Leu Ile Trp Asn Phe Ala Asp Phe Met Thr Glu Gln Ser Pro
                565                 570                 575

Thr Arg Val Leu Gly Asn Lys Lys Gly Ile Phe Thr Arg Gln Arg Gln
                580                 585                 590

Pro Lys Ser Ala Ala Phe Leu Leu Arg Glu Arg Tyr Trp Lys Ile Ala
595                 600                 605

Asn Glu Thr Arg Tyr Pro His Ser Val Ala Lys Ser Gln Cys Leu Glu
610                 615                 620

Asn Ser Leu Phe Thr
625

<210> SEQ ID NO 3
<211> LENGTH: 35
<212> TYPE: DNA
<213> ORGANISM: Homo sapiens
<220> FEATURE:
<221> NAME/KEY: misc_feature
<223> OTHER INFORMATION: PRIMER SEQUENCE

<400> SEQUENCE: 3

```
gaggcaaccg gtctgcaggg cgggatgctg taccc                              35
```

<210> SEQ ID NO 4
<211> LENGTH: 44
<212> TYPE: DNA
<213> ORGANISM: Homo sapiens
<220> FEATURE:
<221> NAME/KEY: misc_feature
<223> OTHER INFORMATION: PRIMER SEQUENCE

<400> SEQUENCE: 4

```
tctagagaat tcctcgagtc aagtaaacag gctgttttcc aaac                    44
```

<210> SEQ ID NO 5
<211> LENGTH: 52
<212> TYPE: DNA
<213> ORGANISM: Homo sapiens
<220> FEATURE:
<221> NAME/KEY: misc_feature
<223> OTHER INFORMATION: PRIMER SEQUENCE

<400> SEQUENCE: 5

```
attaggtacc tgatcagaag aggaggaaga agaggccgag gcagaaaccg gt           52
```

<210> SEQ ID NO 6
<211> LENGTH: 25
<212> TYPE: DNA
<213> ORGANISM: Homo sapiens
<220> FEATURE:
<221> NAME/KEY: misc_feature
<223> OTHER INFORMATION: PRIMER SEQUENCE

<400> SEQUENCE: 6

```
tgcggggcac cggtttctgc ctcgg                                         25
```

<210> SEQ ID NO 7
<211> LENGTH: 58
<212> TYPE: DNA
<213> ORGANISM: Homo sapiens
<220> FEATURE:
<221> NAME/KEY: misc_feature
<223> OTHER INFORMATION: PRIMER SEQUENCE

<400> SEQUENCE: 7

```
attaggtacc tgatcagaag aggaagagga ggaagaagag gccgaggcag aaaccggt     58
```

<210> SEQ ID NO 8
<211> LENGTH: 51
<212> TYPE: DNA
<213> ORGANISM: Homo sapiens
<220> FEATURE:
<221> NAME/KEY: misc_feature
<223> OTHER INFORMATION: PRIMER SEQUENCE

<400> SEQUENCE: 8

```
attaggtacc tgatcagatg atgatgatga tgatgccgag gcagaaaccg g            51
```

<210> SEQ ID NO 9
<211> LENGTH: 57
<212> TYPE: DNA
<213> ORGANISM: Homo sapiens
<220> FEATURE:
<221> NAME/KEY: misc_feature
<223> OTHER INFORMATION: PRIMER SEQUENCE

<400> SEQUENCE: 9

```
attaggtacc tgatcagatg atgatgatga tgatgatgat gccgaggcag aaaccgg      57
```

-continued

```
<210> SEQ ID NO 10
<211> LENGTH: 1983
<212> TYPE: DNA
<213> ORGANISM: Homo sapiens
<220> FEATURE:
<221> NAME/KEY: CDS
<222> LOCATION: (1)..(1983)

<400> SEQUENCE: 10
```

| | | | | | | | | | | | | | | | | |
|---|---|---|---|---|---|---|---|---|---|---|---|---|---|---|---|---|
| atg | cgg | ggt | ccg | agc | ggg | gct | ctg | tgg | ctg | ctc | ctg | gct | ctg | cgc | acc | 48 |
| Met | Arg | Gly | Pro | Ser | Gly | Ala | Leu | Trp | Leu | Leu | Leu | Ala | Leu | Arg | Thr | |
| 1 | | | | 5 | | | | | 10 | | | | | 15 | | |
| gtg | ctc | gga | tca | gaa | gag | gag | gaa | gag | gcc | gag | gca | gaa | acc | ggt | | 96 |
| Val | Leu | Gly | Ser | Glu | Glu | Glu | Glu | Glu | Ala | Glu | Ala | Glu | Thr | Gly | | |
| | | 20 | | | | | 25 | | | | | 30 | | | | |
| ctg | cag | ggc | ggg | atg | ctg | tac | ccc | cag | gag | agc | ccg | tcg | cgg | gag | tgc | 144 |
| Leu | Gln | Gly | Gly | Met | Leu | Tyr | Pro | Gln | Glu | Ser | Pro | Ser | Arg | Glu | Cys | |
| | | 35 | | | | | 40 | | | | | 45 | | | | |
| aag | gag | ctg | gac | ggc | ctc | tgg | agc | ttc | cgc | gcc | gac | ttc | tct | gac | aac | 192 |
| Lys | Glu | Leu | Asp | Gly | Leu | Trp | Ser | Phe | Arg | Ala | Asp | Phe | Ser | Asp | Asn | |
| 50 | | | | | 55 | | | | | 60 | | | | | | |
| cga | cgc | cgg | ggc | ttc | gag | gag | cag | tgg | tac | cgg | cgg | ccg | ctg | tgg | gag | 240 |
| Arg | Arg | Arg | Gly | Phe | Glu | Glu | Gln | Trp | Tyr | Arg | Arg | Pro | Leu | Trp | Glu | |
| 65 | | | | | 70 | | | | | 75 | | | | | 80 | |
| tca | ggc | ccc | acc | gtg | gac | atg | cca | gtt | ccc | tcc | agc | ttc | aat | gac | atc | 288 |
| Ser | Gly | Pro | Thr | Val | Asp | Met | Pro | Val | Pro | Ser | Ser | Phe | Asn | Asp | Ile | |
| | | | | 85 | | | | | 90 | | | | | 95 | | |
| agc | cag | gac | tgg | cgt | ctg | cgg | cat | ttt | gtc | ggc | tgg | gtg | tgg | tac | gaa | 336 |
| Ser | Gln | Asp | Trp | Arg | Leu | Arg | His | Phe | Val | Gly | Trp | Val | Trp | Tyr | Glu | |
| | | | 100 | | | | | 105 | | | | | 110 | | | |
| cgg | gag | gtg | atc | ctg | ccg | gag | cga | tgg | acc | cag | gac | ctg | cgc | aca | aga | 384 |
| Arg | Glu | Val | Ile | Leu | Pro | Glu | Arg | Trp | Thr | Gln | Asp | Leu | Arg | Thr | Arg | |
| | | 115 | | | | | 120 | | | | | 125 | | | | |
| gtg | gtg | ctg | agg | att | ggc | agt | gcc | cat | tcc | tat | gcc | atc | gtg | tgg | gtg | 432 |
| Val | Val | Leu | Arg | Ile | Gly | Ser | Ala | His | Ser | Tyr | Ala | Ile | Val | Trp | Val | |
| | | 130 | | | | | 135 | | | | | 140 | | | | |
| aat | ggg | gtc | gac | acg | cta | gag | cat | gag | ggg | ggc | tac | ctc | ccc | ttc | gag | 480 |
| Asn | Gly | Val | Asp | Thr | Leu | Glu | His | Glu | Gly | Gly | Tyr | Leu | Pro | Phe | Glu | |
| 145 | | | | | 150 | | | | | 155 | | | | | 160 | |
| gcc | gac | atc | agc | aac | ctg | gtc | cag | gtg | ggg | ccc | ctg | ccc | tcc | cgg | ctc | 528 |
| Ala | Asp | Ile | Ser | Asn | Leu | Val | Gln | Val | Gly | Pro | Leu | Pro | Ser | Arg | Leu | |
| | | | | 165 | | | | | 170 | | | | | 175 | | |
| cga | atc | act | atc | gcc | atc | aac | aac | aca | ctc | acc | ccc | acc | acc | ctg | cca | 576 |
| Arg | Ile | Thr | Ile | Ala | Ile | Asn | Asn | Thr | Leu | Thr | Pro | Thr | Thr | Leu | Pro | |
| | | | 180 | | | | | 185 | | | | | 190 | | | |
| cca | ggg | acc | atc | caa | tac | ctg | act | gac | acc | tcc | aag | tat | ccc | aag | ggt | 624 |
| Pro | Gly | Thr | Ile | Gln | Tyr | Leu | Thr | Asp | Thr | Ser | Lys | Tyr | Pro | Lys | Gly | |
| | | 195 | | | | | 200 | | | | | 205 | | | | |
| tac | ttt | gtc | cag | aac | aca | tat | ttt | gac | ttt | ttc | aac | tac | gct | gga | ctg | 672 |
| Tyr | Phe | Val | Gln | Asn | Thr | Tyr | Phe | Asp | Phe | Phe | Asn | Tyr | Ala | Gly | Leu | |
| | 210 | | | | | 215 | | | | | 220 | | | | | |
| cag | cgg | tct | gta | ctt | ctg | tac | acg | aca | ccc | acc | acc | tac | atc | gat | gac | 720 |
| Gln | Arg | Ser | Val | Leu | Leu | Tyr | Thr | Thr | Pro | Thr | Thr | Tyr | Ile | Asp | Asp | |
| 225 | | | | | 230 | | | | | 235 | | | | | 240 | |
| atc | acc | gtc | acc | acc | agc | gtg | gag | caa | gac | agt | ggg | ctg | gtg | aat | tac | 768 |
| Ile | Thr | Val | Thr | Thr | Ser | Val | Glu | Gln | Asp | Ser | Gly | Leu | Val | Asn | Tyr | |
| | | | | 245 | | | | | 250 | | | | | 255 | | |
| cag | atc | tct | gtc | aag | ggc | agt | aac | ctg | ttc | aag | ttg | gaa | gtg | cgt | ctt | 816 |
| Gln | Ile | Ser | Val | Lys | Gly | Ser | Asn | Leu | Phe | Lys | Leu | Glu | Val | Arg | Leu | |
| | | | 260 | | | | | 265 | | | | | 270 | | | |
| ttg | gat | gca | gaa | aac | aaa | gtc | gtg | gcg | aat | ggg | act | ggg | acc | cag | ggc | 864 |

```
                Leu Asp Ala Glu Asn Lys Val Ala Asn Gly Thr Gly Thr Gln Gly
                    275                 280                 285 caa ctt aag gtg cca ggt gtc agc ctc tgg tgg ccg tac ctg atg cac        912
Gln Leu Lys Val Pro Gly Val Ser Leu Trp Trp Pro Tyr Leu Met His
    290                 295                 300 gaa cgc cct gcc tat ctg tat tca ttg gag gtg cag ctg act gca cag        960
Glu Arg Pro Ala Tyr Leu Tyr Ser Leu Glu Val Gln Leu Thr Ala Gln
305                 310                 315                 320 acg tca ctg ggg cct gtg tct gac ttc tac aca ctc cct gtg ggg atc       1008
Thr Ser Leu Gly Pro Val Ser Asp Phe Tyr Thr Leu Pro Val Gly Ile
                325                 330                 335 cgc act gtg gct gtc acc aag agc cag ttc ctc atc aat ggg aaa cct       1056
Arg Thr Val Ala Val Thr Lys Ser Gln Phe Leu Ile Asn Gly Lys Pro
            340                 345                 350 ttc tat ttc cac ggt gtc aac aag cat gag gat gcg gac atc cga ggg       1104
Phe Tyr Phe His Gly Val Asn Lys His Glu Asp Ala Asp Ile Arg Gly
        355                 360                 365 aag ggc ttc gac tgg ccg ctg ctg gtg aag gac ttc aac ctg ctt cgc       1152
Lys Gly Phe Asp Trp Pro Leu Leu Val Lys Asp Phe Asn Leu Leu Arg
370                 375                 380 tgg ctt ggt gcc aac gct ttc cgt acc agc cac tac ccc tat gca gag       1200
Trp Leu Gly Ala Asn Ala Phe Arg Thr Ser His Tyr Pro Tyr Ala Glu
385                 390                 395                 400 gaa gtg atg cag atg tgt gac cgc tat ggg att gtg gtc atc gat gag       1248
Glu Val Met Gln Met Cys Asp Arg Tyr Gly Ile Val Val Ile Asp Glu
                405                 410                 415 tgt ccc ggc gtg ggc ctg gcg ctg ccg cag ttc ttc aac aac gtt tct       1296
Cys Pro Gly Val Gly Leu Ala Leu Pro Gln Phe Phe Asn Asn Val Ser
            420                 425                 430 ctg cat cac cac atg cag gtg atg gaa gaa gtg gtg cgt agg gac aag       1344
Leu His His His Met Gln Val Met Glu Glu Val Val Arg Arg Asp Lys
        435                 440                 445 aac cac ccc gcg gtc gtg atg tgg tct gtg gcc aac gag cct gcg tcc       1392
Asn His Pro Ala Val Val Met Trp Ser Val Ala Asn Glu Pro Ala Ser
        450                 455                 460 cac cta gaa tct gct ggc tac tac ttg aag atg gtg atc gct cac acc       1440
His Leu Glu Ser Ala Gly Tyr Tyr Leu Lys Met Val Ile Ala His Thr
465                 470                 475                 480 aaa tcc ttg gac ccc tcc cgg cct gtg acc ttt gtg agc aac tct aac       1488
Lys Ser Leu Asp Pro Ser Arg Pro Val Thr Phe Val Ser Asn Ser Asn
                485                 490                 495 tat gca gca gac aag ggg gct ccg tat gtg gat gtg atc tgt ttg aac       1536
Tyr Ala Ala Asp Lys Gly Ala Pro Tyr Val Asp Val Ile Cys Leu Asn
            500                 505                 510 agc tac tac tct tgg tat cac gac tac ggg cac ctg gag ttg att cag       1584
Ser Tyr Tyr Ser Trp Tyr His Asp Tyr Gly His Leu Glu Leu Ile Gln
        515                 520                 525 ctg cag ctg gcc acc cag ttt gag aac tgg tat aag aag tat cag aag       1632
Leu Gln Leu Ala Thr Gln Phe Glu Asn Trp Tyr Lys Lys Tyr Gln Lys
530                 535                 540 ccc att att cag agc gag tat gga gca gaa acg att gca ggg ttt cac       1680
Pro Ile Ile Gln Ser Glu Tyr Gly Ala Glu Thr Ile Ala Gly Phe His
545                 550                 555                 560 cag gat cca cct ctg atg ttc act gaa gag tac cag aaa agt ctg cta       1728
Gln Asp Pro Pro Leu Met Phe Thr Glu Glu Tyr Gln Lys Ser Leu Leu
                565                 570                 575 gag cag tac cat ctg ggt ctg gat caa aaa cgc aga aaa tat gtg gtt       1776
Glu Gln Tyr His Leu Gly Leu Asp Gln Lys Arg Arg Lys Tyr Val Val
            580                 585                 590 gga gag ctc att tgg aat ttt gcc gat ttc atg act gaa cag tca ccg       1824
```

```
Gly Glu Leu Ile Trp Asn Phe Ala Asp Phe Met Thr Glu Gln Ser Pro
        595                 600                 605 acg aga gtg ctg ggg aat aaa aag ggg atc ttc act cgg cag aga caa    1872
Thr Arg Val Leu Gly Asn Lys Lys Gly Ile Phe Thr Arg Gln Arg Gln
610                 615                 620 cca aaa agt gca gcg ttc ctt ttg cga gag aga tac tgg aag att gcc    1920
Pro Lys Ser Ala Ala Phe Leu Leu Arg Glu Arg Tyr Trp Lys Ile Ala
625                 630                 635                 640 aat gaa acc agg tat ccc cac tca gta gcc aag tca caa tgt ttg gaa    1968
Asn Glu Thr Arg Tyr Pro His Ser Val Ala Lys Ser Gln Cys Leu Glu
            645                 650                 655 aac agc ccg ttt act                                                 1983
Asn Ser Pro Phe Thr
        660

<210> SEQ ID NO 11
<211> LENGTH: 661
<212> TYPE: PRT
<213> ORGANISM: Homo sapiens

<400> SEQUENCE: 11

Met Arg Gly Pro Ser Gly Ala Leu Trp Leu Leu Leu Ala Leu Arg Thr
1               5                   10                  15

Val Leu Gly Ser Glu Glu Glu Glu Ala Glu Ala Glu Thr Gly
            20                  25                  30

Leu Gln Gly Gly Met Leu Tyr Pro Gln Glu Ser Pro Ser Arg Glu Cys
            35                  40                  45

Lys Glu Leu Asp Gly Leu Trp Ser Phe Arg Ala Asp Phe Ser Asp Asn
50                  55                  60

Arg Arg Arg Gly Phe Glu Glu Gln Trp Tyr Arg Arg Pro Leu Trp Glu
65                  70                  75                  80

Ser Gly Pro Thr Val Asp Met Pro Val Pro Ser Ser Phe Asn Asp Ile
                85                  90                  95

Ser Gln Asp Trp Arg Leu Arg His Phe Val Gly Trp Val Trp Tyr Glu
            100                 105                 110

Arg Glu Val Ile Leu Pro Glu Arg Trp Thr Gln Asp Leu Arg Thr Arg
            115                 120                 125

Val Val Leu Arg Ile Gly Ser Ala His Ser Tyr Ala Ile Val Trp Val
        130                 135                 140

Asn Gly Val Asp Thr Leu Glu His Glu Gly Gly Tyr Leu Pro Phe Glu
145                 150                 155                 160

Ala Asp Ile Ser Asn Leu Val Gln Val Gly Pro Leu Pro Ser Arg Leu
                165                 170                 175

Arg Ile Thr Ile Ala Ile Asn Asn Thr Leu Thr Pro Thr Thr Leu Pro
            180                 185                 190

Pro Gly Thr Ile Gln Tyr Leu Thr Asp Thr Ser Lys Tyr Pro Lys Gly
            195                 200                 205

Tyr Phe Val Gln Asn Thr Tyr Phe Asp Phe Phe Asn Tyr Ala Gly Leu
        210                 215                 220

Gln Arg Ser Val Leu Leu Tyr Thr Thr Pro Thr Thr Tyr Ile Asp Asp
225                 230                 235                 240

Ile Thr Val Thr Thr Ser Val Glu Gln Asp Ser Gly Leu Val Asn Tyr
                245                 250                 255

Gln Ile Ser Val Lys Gly Ser Asn Leu Phe Lys Leu Glu Val Arg Leu
            260                 265                 270

Leu Asp Ala Glu Asn Lys Val Val Ala Asn Gly Thr Gly Thr Gln Gly
        275                 280                 285
```

Gln Leu Lys Val Pro Gly Val Ser Leu Trp Trp Pro Tyr Leu Met His
    290                 295                 300

Glu Arg Pro Ala Tyr Leu Tyr Ser Leu Glu Val Gln Leu Thr Ala Gln
305                 310                 315                 320

Thr Ser Leu Gly Pro Val Ser Asp Phe Tyr Thr Leu Pro Val Gly Ile
                325                 330                 335

Arg Thr Val Ala Val Thr Lys Ser Gln Phe Leu Ile Asn Gly Lys Pro
            340                 345                 350

Phe Tyr Phe His Gly Val Asn Lys His Glu Asp Ala Asp Ile Arg Gly
        355                 360                 365

Lys Gly Phe Asp Trp Pro Leu Leu Val Lys Asp Phe Asn Leu Leu Arg
370                 375                 380

Trp Leu Gly Ala Asn Ala Phe Arg Thr Ser His Tyr Pro Tyr Ala Glu
385                 390                 395                 400

Glu Val Met Gln Met Cys Asp Arg Tyr Gly Ile Val Val Ile Asp Glu
                405                 410                 415

Cys Pro Gly Val Gly Leu Ala Leu Pro Gln Phe Phe Asn Asn Val Ser
                420                 425                 430

Leu His His His Met Gln Val Met Glu Glu Val Val Arg Arg Asp Lys
            435                 440                 445

Asn His Pro Ala Val Val Met Trp Ser Val Ala Asn Glu Pro Ala Ser
450                 455                 460

His Leu Glu Ser Ala Gly Tyr Tyr Leu Lys Met Val Ile Ala His Thr
465                 470                 475                 480

Lys Ser Leu Asp Pro Ser Arg Pro Val Thr Phe Val Ser Asn Ser Asn
                485                 490                 495

Tyr Ala Ala Asp Lys Gly Ala Pro Tyr Val Asp Val Ile Cys Leu Asn
                500                 505                 510

Ser Tyr Tyr Ser Trp Tyr His Asp Tyr Gly His Leu Glu Leu Ile Gln
            515                 520                 525

Leu Gln Leu Ala Thr Gln Phe Glu Asn Trp Tyr Lys Lys Tyr Gln Lys
    530                 535                 540

Pro Ile Ile Gln Ser Glu Tyr Gly Ala Glu Thr Ile Ala Gly Phe His
545                 550                 555                 560

Gln Asp Pro Pro Leu Met Phe Thr Glu Glu Tyr Gln Lys Ser Leu Leu
                565                 570                 575

Glu Gln Tyr His Leu Gly Leu Asp Gln Lys Arg Arg Lys Tyr Val Val
                580                 585                 590

Gly Glu Leu Ile Trp Asn Phe Ala Asp Phe Met Thr Glu Gln Ser Pro
            595                 600                 605

Thr Arg Val Leu Gly Asn Lys Lys Gly Ile Phe Thr Arg Gln Arg Gln
    610                 615                 620

Pro Lys Ser Ala Ala Phe Leu Leu Arg Glu Arg Tyr Trp Lys Ile Ala
625                 630                 635                 640

Asn Glu Thr Arg Tyr Pro His Ser Val Ala Lys Ser Gln Cys Leu Glu
                645                 650                 655

Asn Ser Pro Phe Thr
            660

<210> SEQ ID NO 12
<211> LENGTH: 1989
<212> TYPE: DNA
<213> ORGANISM: Homo sapiens
<220> FEATURE:
<221> NAME/KEY: CDS -continued

<222> LOCATION: (1)..(1989)

<400> SEQUENCE: 12

```
atg cgg ggt ccg agc ggg gct ctg tgg ctg ctc ctg gct ctg cgc acc      48
Met Arg Gly Pro Ser Gly Ala Leu Trp Leu Leu Leu Ala Leu Arg Thr
1               5                   10                  15 gtg ctc gga tca gaa gag gag gag gaa gaa gag gcc gag gca gaa          96
Val Leu Gly Ser Glu Glu Glu Glu Glu Glu Glu Ala Glu Ala Glu
            20                  25                  30 acc ggt ctg cag ggc ggg atg ctg tac ccc cag gag agc ccg tcg cgg     144
Thr Gly Leu Gln Gly Gly Met Leu Tyr Pro Gln Glu Ser Pro Ser Arg
        35                  40                  45 gag tgc aag gag ctg gac ggc ctc tgg agc ttc cgc gcc gac ttc tct     192
Glu Cys Lys Glu Leu Asp Gly Leu Trp Ser Phe Arg Ala Asp Phe Ser
    50                  55                  60 gac aac cga cgc cgg ggc ttc gag gag cag tgg tac cgg cgg ccg ctg     240
Asp Asn Arg Arg Arg Gly Phe Glu Glu Gln Trp Tyr Arg Arg Pro Leu
65                  70                  75                  80 tgg gag tca ggc ccc acc gtg gac atg cca gtt ccc tcc agc ttc aat     288
Trp Glu Ser Gly Pro Thr Val Asp Met Pro Val Pro Ser Ser Phe Asn
                85                  90                  95 gac atc agc cag gac tgg cgt ctg cgg cat ttt gtc ggc tgg gtg tgg     336
Asp Ile Ser Gln Asp Trp Arg Leu Arg His Phe Val Gly Trp Val Trp
            100                 105                 110 tac gaa cgg gag gtg atc ctg ccg gag cga tgg acc cag gac ctg cgc     384
Tyr Glu Arg Glu Val Ile Leu Pro Glu Arg Trp Thr Gln Asp Leu Arg
        115                 120                 125 aca aga gtg gtg ctg agg att ggc agt gcc cat tcc tat gcc atc gtg     432
Thr Arg Val Val Leu Arg Ile Gly Ser Ala His Ser Tyr Ala Ile Val
    130                 135                 140 tgg gtg aat ggg gtc gac acg cta gag cat gag ggg ggc tac ctc ccc     480
Trp Val Asn Gly Val Asp Thr Leu Glu His Glu Gly Gly Tyr Leu Pro
145                 150                 155                 160 ttc gag gcc gac atc agc aac ctg gtc cag gtg ggg ccc ctg ccc tcc     528
Phe Glu Ala Asp Ile Ser Asn Leu Val Gln Val Gly Pro Leu Pro Ser
                165                 170                 175 cgg ctc cga atc act atc gcc atc aac aac aca ctc acc ccc acc acc     576
Arg Leu Arg Ile Thr Ile Ala Ile Asn Asn Thr Leu Thr Pro Thr Thr
            180                 185                 190 ctg cca cca ggg acc atc caa tac ctg act gac acc tcc aag tat ccc     624
Leu Pro Pro Gly Thr Ile Gln Tyr Leu Thr Asp Thr Ser Lys Tyr Pro
        195                 200                 205 aag ggt tac ttt gtc cag aac aca tat ttt gac ttt ttc aac tac gct     672
Lys Gly Tyr Phe Val Gln Asn Thr Tyr Phe Asp Phe Phe Asn Tyr Ala
    210                 215                 220 gga ctg cag cgg tct gta ctt ctg tac acg aca ccc acc acc tac atc     720
Gly Leu Gln Arg Ser Val Leu Leu Tyr Thr Thr Pro Thr Thr Tyr Ile
225                 230                 235                 240 gat gac atc acc gtc acc acc agc gtg gag caa gac agt ggg ctg gtg     768
Asp Asp Ile Thr Val Thr Thr Ser Val Glu Gln Asp Ser Gly Leu Val
                245                 250                 255 aat tac cag atc tct gtc aag ggc agt aac ctg ttc aag ttg gaa gtg     816
Asn Tyr Gln Ile Ser Val Lys Gly Ser Asn Leu Phe Lys Leu Glu Val
            260                 265                 270 cgt ctt ttg gat gca gaa aac aaa gtc gtg gcg aat ggg act ggg acc     864
Arg Leu Leu Asp Ala Glu Asn Lys Val Val Ala Asn Gly Thr Gly Thr
        275                 280                 285 cag ggc caa ctt aag gtg cca ggt gtc agc ctc tgg tgg ccg tac ctg     912
Gln Gly Gln Leu Lys Val Pro Gly Val Ser Leu Trp Trp Pro Tyr Leu
    290                 295                 300
```

|  |  |  |  |  |  |  |  |  |  |  |  |  |  |  |  |
|---|---|---|---|---|---|---|---|---|---|---|---|---|---|---|---|
| atg | cac | gaa | cgc | cct | gcc | tat | ctg | tat | tca | ttg | gag | gtg | cag | ctg | act | 960 |
| Met | His | Glu | Arg | Pro | Ala | Tyr | Leu | Tyr | Ser | Leu | Glu | Val | Gln | Leu | Thr |
| 305 |  |  |  | 310 |  |  |  |  | 315 |  |  |  |  | 320 |  |

```
atg cac gaa cgc cct gcc tat ctg tat tca ttg gag gtg cag ctg act      960
Met His Glu Arg Pro Ala Tyr Leu Tyr Ser Leu Glu Val Gln Leu Thr
305                 310                 315                 320 gca cag acg tca ctg ggg cct gtg tct gac ttc tac aca ctc cct gtg     1008
Ala Gln Thr Ser Leu Gly Pro Val Ser Asp Phe Tyr Thr Leu Pro Val
                325                 330                 335 ggg atc cgc act gtg gct gtc acc aag agc cag ttc ctc atc aat ggg     1056
Gly Ile Arg Thr Val Ala Val Thr Lys Ser Gln Phe Leu Ile Asn Gly
        340                 345                 350 aaa cct ttc tat ttc cac ggt gtc aac aag cat gag gat gcg gac atc     1104
Lys Pro Phe Tyr Phe His Gly Val Asn Lys His Glu Asp Ala Asp Ile
355                 360                 365 cga ggg aag ggc ttc gac tgg ccg ctg ctg gtg aag gac ttc aac ctg     1152
Arg Gly Lys Gly Phe Asp Trp Pro Leu Leu Val Lys Asp Phe Asn Leu
    370                 375                 380 ctt cgc tgg ctt ggt gcc aac gct ttc cgt acc agc cac tac ccc tat     1200
Leu Arg Trp Leu Gly Ala Asn Ala Phe Arg Thr Ser His Tyr Pro Tyr
385                 390                 395                 400 gca gag gaa gtg atg cag atg tgt gac cgc tat ggg att gtg gtc atc     1248
Ala Glu Glu Val Met Gln Met Cys Asp Arg Tyr Gly Ile Val Val Ile
                405                 410                 415 gat gag tgt ccc ggc gtg ggc ctg gcg ctg ccg cag ttc ttc aac aac     1296
Asp Glu Cys Pro Gly Val Gly Leu Ala Leu Pro Gln Phe Phe Asn Asn
        420                 425                 430 gtt tct ctg cat cac cac atg cag gtg atg gaa gaa gtg gtg cgt agg     1344
Val Ser Leu His His His Met Gln Val Met Glu Glu Val Val Arg Arg
435                 440                 445 gac aag aac cac ccc gcg gtc gtg atg tgg tct gtg gcc aac gag cct     1392
Asp Lys Asn His Pro Ala Val Val Met Trp Ser Val Ala Asn Glu Pro
    450                 455                 460 gcg tcc cac cta gaa tct gct ggc tac tac ttg aag atg gtg atc gct     1440
Ala Ser His Leu Glu Ser Ala Gly Tyr Tyr Leu Lys Met Val Ile Ala
465                 470                 475                 480 cac acc aaa tcc ttg gac ccc tcc cgg cct gtg acc ttt gtg agc aac     1488
His Thr Lys Ser Leu Asp Pro Ser Arg Pro Val Thr Phe Val Ser Asn
                485                 490                 495 tct aac tat gca gca gac aag ggg gct ccg tat gtg gat gtg atc tgt     1536
Ser Asn Tyr Ala Ala Asp Lys Gly Ala Pro Tyr Val Asp Val Ile Cys
        500                 505                 510 ttg aac agc tac tac tct tgg tat cac gac tac ggg cac ctg gag ttg     1584
Leu Asn Ser Tyr Tyr Ser Trp Tyr His Asp Tyr Gly His Leu Glu Leu
515                 520                 525 att cag ctg cag ctg gcc acc cag ttt gag aac tgg tat aag aag tat     1632
Ile Gln Leu Gln Leu Ala Thr Gln Phe Glu Asn Trp Tyr Lys Lys Tyr
    530                 535                 540 cag aag ccc att att cag agc gag tat gga gca gaa acg att gca ggg     1680
Gln Lys Pro Ile Ile Gln Ser Glu Tyr Gly Ala Glu Thr Ile Ala Gly
545                 550                 555                 560 ttt cac cag gat cca cct ctg atg ttc act gaa gag tac cag aaa agt     1728
Phe His Gln Asp Pro Pro Leu Met Phe Thr Glu Glu Tyr Gln Lys Ser
                565                 570                 575 ctg cta gag cag tac cat ctg ggt ctg gat caa aaa cgc aga aaa tat     1776
Leu Leu Glu Gln Tyr His Leu Gly Leu Asp Gln Lys Arg Arg Lys Tyr
        580                 585                 590 gtg gtt gga gag ctc att tgg aat ttt gcc gat ttc atg act gaa cag     1824
Val Val Gly Glu Leu Ile Trp Asn Phe Ala Asp Phe Met Thr Glu Gln
595                 600                 605 tca ccg acg aga gtg ctg ggg aat aaa aag ggg atc ttc act cgg cag     1872
Ser Pro Thr Arg Val Leu Gly Asn Lys Lys Gly Ile Phe Thr Arg Gln
    610                 615                 620
```

-continued

| aga | caa | cca | aaa | agt | gca | gcg | ttc | ctt | ttg | cga | gag | aga | tac | tgg | aag | 1920 |
| Arg | Gln | Pro | Lys | Ser | Ala | Ala | Phe | Leu | Leu | Arg | Glu | Arg | Tyr | Trp | Lys | |
| 625 | | | | 630 | | | | | 635 | | | | | 640 | | |

| att | gcc | aat | gaa | acc | agg | tat | ccc | cac | tca | gta | gcc | aag | tca | caa | tgt | 1968 |
| Ile | Ala | Asn | Glu | Thr | Arg | Tyr | Pro | His | Ser | Val | Ala | Lys | Ser | Gln | Cys | |
| | | | | 645 | | | | | 650 | | | | | 655 | | |

| ttg | gaa | aac | agc | ccg | ttt | act | | | | | | | | | | 1989 |
| Leu | Glu | Asn | Ser | Pro | Phe | Thr | | | | | | | | | | |
| | | 660 | | | | | | | | | | | | | | |

```
<210> SEQ ID NO 13
<211> LENGTH: 663
<212> TYPE: PRT
<213> ORGANISM: Homo sapiens

<400> SEQUENCE: 13
```

Met Arg Gly Pro Ser Gly Ala Leu Trp Leu Leu Ala Leu Arg Thr
1               5                   10                  15

Val Leu Gly Ser Glu Glu Glu Glu Glu Glu Ala Glu Ala Glu
            20                  25                  30

Thr Gly Leu Gln Gly Gly Met Leu Tyr Pro Gln Glu Ser Pro Ser Arg
            35                  40                  45

Glu Cys Lys Glu Leu Asp Gly Leu Trp Ser Phe Arg Ala Asp Phe Ser
        50                  55                  60

Asp Asn Arg Arg Arg Gly Phe Glu Glu Gln Trp Tyr Arg Arg Pro Leu
65                  70                  75                  80

Trp Glu Ser Gly Pro Thr Val Asp Met Pro Val Pro Ser Ser Phe Asn
            85                  90                  95

Asp Ile Ser Gln Asp Trp Arg Leu Arg His Phe Val Gly Trp Val Trp
            100                 105                 110

Tyr Glu Arg Glu Val Ile Leu Pro Glu Arg Trp Thr Gln Asp Leu Arg
            115                 120                 125

Thr Arg Val Val Leu Arg Ile Gly Ser Ala His Ser Tyr Ala Ile Val
130                 135                 140

Trp Val Asn Gly Val Asp Thr Leu Glu His Glu Gly Gly Tyr Leu Pro
145                 150                 155                 160

Phe Glu Ala Asp Ile Ser Asn Leu Val Gln Val Gly Pro Leu Pro Ser
            165                 170                 175

Arg Leu Arg Ile Thr Ile Ala Ile Asn Asn Thr Leu Thr Pro Thr Thr
            180                 185                 190

Leu Pro Pro Gly Thr Ile Gln Tyr Leu Thr Asp Thr Ser Lys Tyr Pro
            195                 200                 205

Lys Gly Tyr Phe Val Gln Asn Thr Tyr Phe Asp Phe Phe Asn Tyr Ala
            210                 215                 220

Gly Leu Gln Arg Ser Val Leu Leu Tyr Thr Thr Pro Thr Thr Tyr Ile
225                 230                 235                 240

Asp Asp Ile Thr Val Thr Thr Ser Val Glu Gln Asp Ser Gly Leu Val
            245                 250                 255

Asn Tyr Gln Ile Ser Val Lys Gly Ser Asn Leu Phe Lys Leu Glu Val
            260                 265                 270

Arg Leu Leu Asp Ala Glu Asn Lys Val Val Ala Asn Gly Thr Gly Thr
            275                 280                 285

Gln Gly Gln Leu Lys Val Pro Gly Val Ser Leu Trp Trp Pro Tyr Leu
            290                 295                 300

Met His Glu Arg Pro Ala Tyr Leu Tyr Ser Leu Glu Val Gln Leu Thr
305                 310                 315                 320

-continued

```
Ala Gln Thr Ser Leu Gly Pro Val Ser Asp Phe Tyr Thr Leu Pro Val
            325                 330                 335

Gly Ile Arg Thr Val Ala Val Thr Lys Ser Gln Phe Leu Ile Asn Gly
        340                 345                 350

Lys Pro Phe Tyr Phe His Gly Val Asn Lys His Glu Asp Ala Asp Ile
    355                 360                 365

Arg Gly Lys Gly Phe Asp Trp Pro Leu Leu Val Lys Asp Phe Asn Leu
370                 375                 380

Leu Arg Trp Leu Gly Ala Asn Ala Phe Arg Thr Ser His Tyr Pro Tyr
385                 390                 395                 400

Ala Glu Glu Val Met Gln Met Cys Asp Arg Tyr Gly Ile Val Val Ile
                405                 410                 415

Asp Glu Cys Pro Gly Val Gly Leu Ala Leu Pro Gln Phe Phe Asn Asn
            420                 425                 430

Val Ser Leu His His Met Gln Val Met Glu Val Val Arg Arg
        435                 440                 445

Asp Lys Asn His Pro Ala Val Val Met Trp Ser Val Ala Asn Glu Pro
    450                 455                 460

Ala Ser His Leu Glu Ser Ala Gly Tyr Tyr Leu Lys Met Val Ile Ala
465                 470                 475                 480

His Thr Lys Ser Leu Asp Pro Ser Arg Pro Val Thr Phe Val Ser Asn
                485                 490                 495

Ser Asn Tyr Ala Ala Asp Lys Gly Ala Pro Tyr Val Asp Val Ile Cys
            500                 505                 510

Leu Asn Ser Tyr Tyr Ser Trp Tyr His Asp Tyr Gly His Leu Glu Leu
        515                 520                 525

Ile Gln Leu Gln Leu Ala Thr Gln Phe Glu Asn Trp Tyr Lys Lys Tyr
    530                 535                 540

Gln Lys Pro Ile Ile Gln Ser Glu Tyr Gly Ala Glu Thr Ile Ala Gly
545                 550                 555                 560

Phe His Gln Asp Pro Pro Leu Met Phe Thr Glu Glu Tyr Gln Lys Ser
                565                 570                 575

Leu Leu Glu Gln Tyr His Leu Gly Leu Asp Gln Lys Arg Arg Lys Tyr
            580                 585                 590

Val Val Gly Glu Leu Ile Trp Asn Phe Ala Asp Phe Met Thr Glu Gln
        595                 600                 605

Ser Pro Thr Arg Val Leu Gly Asn Lys Lys Gly Ile Phe Thr Arg Gln
    610                 615                 620

Arg Gln Pro Lys Ser Ala Ala Phe Leu Leu Arg Glu Arg Tyr Trp Lys
625                 630                 635                 640

Ile Ala Asn Glu Thr Arg Tyr Pro His Ser Val Ala Lys Ser Gln Cys
                645                 650                 655

Leu Glu Asn Ser Pro Phe Thr
            660
```

<210> SEQ ID NO 14
<211> LENGTH: 1983
<212> TYPE: DNA
<213> ORGANISM: Homo sapiens
<220> FEATURE:
<221> NAME/KEY: CDS
<222> LOCATION: (1)..(1983)

<400> SEQUENCE: 14

```
atg cgg ggt ccg agc ggg gct ctg tgg ctg ctc ctg gct ctg cgc acc       48
Met Arg Gly Pro Ser Gly Ala Leu Trp Leu Leu Leu Ala Leu Arg Thr
1               5                  10                  15
```

-continued

| | | |
|---|---|---|
| gtg ctc gga tca gat gat gat gat gat gat gcc gag gca gaa acc ggt<br>Val Leu Gly Ser Asp Asp Asp Asp Asp Asp Ala Glu Ala Glu Thr Gly<br>            20                        25                  30 | 96 |
| ctg cag ggc ggg atg ctg tac ccc cag gag agc ccg tcg cgg gag tgc<br>Leu Gln Gly Gly Met Leu Tyr Pro Gln Glu Ser Pro Ser Arg Glu Cys<br>            35                        40                  45 | 144 |
| aag gag ctg gac ggc ctc tgg agc ttc cgc gcc gac ttc tct gac aac<br>Lys Glu Leu Asp Gly Leu Trp Ser Phe Arg Ala Asp Phe Ser Asp Asn<br>50                        55                        60 | 192 |
| cga cgc cgg ggc ttc gag gag cag tgg tac cgg cgg ccg ctg tgg gag<br>Arg Arg Arg Gly Phe Glu Glu Gln Trp Tyr Arg Arg Pro Leu Trp Glu<br>65                        70                        75                  80 | 240 |
| tca ggc ccc acc gtg gac atg cca gtt ccc tcc agc ttc aat gac atc<br>Ser Gly Pro Thr Val Asp Met Pro Val Pro Ser Ser Phe Asn Asp Ile<br>                        85                        90                  95 | 288 |
| agc cag gac tgg cgt ctg cgg cat ttt gtc ggc tgg gtg tgg tac gaa<br>Ser Gln Asp Trp Arg Leu Arg His Phe Val Gly Trp Val Trp Tyr Glu<br>                    100                      105                  110 | 336 |
| cgg gag gtg atc ctg ccg gag cga tgg acc cag gac ctg cgc aca aga<br>Arg Glu Val Ile Leu Pro Glu Arg Trp Thr Gln Asp Leu Arg Thr Arg<br>               115                      120                      125 | 384 |
| gtg gtg ctg agg att ggc agt gcc cat tcc tat gcc atc gtg tgg gtg<br>Val Val Leu Arg Ile Gly Ser Ala His Ser Tyr Ala Ile Val Trp Val<br>        130                      135                      140 | 432 |
| aat ggg gtc gac acg cta gag cat gag ggg ggc tac ctc ccc ttc gag<br>Asn Gly Val Asp Thr Leu Glu His Glu Gly Gly Tyr Leu Pro Phe Glu<br>145                        150                      155                  160 | 480 |
| gcc gac atc agc aac ctg gtc cag gtg ggg ccc ctg ccc tcc cgg ctc<br>Ala Asp Ile Ser Asn Leu Val Gln Val Gly Pro Leu Pro Ser Arg Leu<br>                        165                      170                  175 | 528 |
| cga atc act atc gcc atc aac aac aca ctc acc ccc acc acc ctg cca<br>Arg Ile Thr Ile Ala Ile Asn Asn Thr Leu Thr Pro Thr Thr Leu Pro<br>               180                      185                      190 | 576 |
| cca ggg acc atc caa tac ctg act gac acc tcc aag tat ccc aag ggt<br>Pro Gly Thr Ile Gln Tyr Leu Thr Asp Thr Ser Lys Tyr Pro Lys Gly<br>        195                      200                      205 | 624 |
| tac ttt gtc cag aac aca tat ttt gac ttt ttc aac tac gct gga ctg<br>Tyr Phe Val Gln Asn Thr Tyr Phe Asp Phe Phe Asn Tyr Ala Gly Leu<br>210                        215                      220 | 672 |
| cag cgg tct gta ctt ctg tac acg aca ccc acc acc tac atc gat gac<br>Gln Arg Ser Val Leu Leu Tyr Thr Thr Pro Thr Thr Tyr Ile Asp Asp<br>225                        230                      235                  240 | 720 |
| atc acc gtc acc acc agc gtg gag caa gac agt ggg ctg gtg aat tac<br>Ile Thr Val Thr Thr Ser Val Glu Gln Asp Ser Gly Leu Val Asn Tyr<br>                        245                      250                  255 | 768 |
| cag atc tct gtc aag ggc agt aac ctg ttc aag ttg gaa gtg cgt ctt<br>Gln Ile Ser Val Lys Gly Ser Asn Leu Phe Lys Leu Glu Val Arg Leu<br>        260                      265                      270 | 816 |
| ttg gat gca gaa aac aaa gtc gtg gcg aat ggg act ggg acc cag ggc<br>Leu Asp Ala Glu Asn Lys Val Val Ala Asn Gly Thr Gly Thr Gln Gly<br>               275                      280                      285 | 864 |
| caa ctt aag gtg cca ggt gtc agc ctc tgg tgg ccg tac ctg atg cac<br>Gln Leu Lys Val Pro Gly Val Ser Leu Trp Trp Pro Tyr Leu Met His<br>        290                      295                      300 | 912 |
| gaa cgc cct gcc tat ctg tat tca ttg gag gtg cag ctg act gca cag<br>Glu Arg Pro Ala Tyr Leu Tyr Ser Leu Glu Val Gln Leu Thr Ala Gln<br>305                        310                      315                  320 | 960 |
| acg tca ctg ggg cct gtg tct gac ttc tac aca ctc cct gtg ggg atc<br>Thr Ser Leu Gly Pro Val Ser Asp Phe Tyr Thr Leu Pro Val Gly Ile<br>                        325                      330                  335 | 1008 |

| | |
|---|---|
| cgc act gtg gct gtc acc aag agc cag ttc ctc atc aat ggg aaa cct<br>Arg Thr Val Ala Val Thr Lys Ser Gln Phe Leu Ile Asn Gly Lys Pro<br>                    340                      345                    350 | 1056 |
| ttc tat ttc cac ggt gtc aac aag cat gag gat gcg gac atc cga ggg<br>Phe Tyr Phe His Gly Val Asn Lys His Glu Asp Ala Asp Ile Arg Gly<br>                  355                      360                    365 | 1104 |
| aag ggc ttc gac tgg ccg ctg ctg gtg aag gac ttc aac ctg ctt cgc<br>Lys Gly Phe Asp Trp Pro Leu Leu Val Lys Asp Phe Asn Leu Leu Arg<br>370                      375                    380 | 1152 |
| tgg ctt ggt gcc aac gct ttc cgt acc agc cac tac ccc tat gca gag<br>Trp Leu Gly Ala Asn Ala Phe Arg Thr Ser His Tyr Pro Tyr Ala Glu<br>385                    390                      395                    400 | 1200 |
| gaa gtg atg cag atg tgt gac cgc tat ggg att gtg gtc atc gat gag<br>Glu Val Met Gln Met Cys Asp Arg Tyr Gly Ile Val Val Ile Asp Glu<br>                            405                      410                    415 | 1248 |
| tgt ccc ggc gtg ggc ctg gcg ctg ccg cag ttc ttc aac aac gtt tct<br>Cys Pro Gly Val Gly Leu Ala Leu Pro Gln Phe Phe Asn Asn Val Ser<br>                  420                      425                    430 | 1296 |
| ctg cat cac cac atg cag gtg atg gaa gaa gtg gtg cgt agg gac aag<br>Leu His His His Met Gln Val Met Glu Glu Val Val Arg Arg Asp Lys<br>                      435                      440                    445 | 1344 |
| aac cac ccc gcg gtc gtg atg tgg tct gtg gcc aac gag cct gcg tcc<br>Asn His Pro Ala Val Val Met Trp Ser Val Ala Asn Glu Pro Ala Ser<br>450                      455                    460 | 1392 |
| cac cta gaa tct gct ggc tac tac ttg aag atg gtg atc gct cac acc<br>His Leu Glu Ser Ala Gly Tyr Tyr Leu Lys Met Val Ile Ala His Thr<br>465                      470                      475                    480 | 1440 |
| aaa tcc ttg gac ccc tcc cgg cct gtg acc ttt gtg agc aac tct aac<br>Lys Ser Leu Asp Pro Ser Arg Pro Val Thr Phe Val Ser Asn Ser Asn<br>                          485                      490                    495 | 1488 |
| tat gca gca gac aag ggg gct ccg tat gtg gat gtg atc tgt ttg aac<br>Tyr Ala Ala Asp Lys Gly Ala Pro Tyr Val Asp Val Ile Cys Leu Asn<br>                  500                      505                    510 | 1536 |
| agc tac tac tct tgg tat cac gac tac ggg cac ctg gag ttg att cag<br>Ser Tyr Tyr Ser Trp Tyr His Asp Tyr Gly His Leu Glu Leu Ile Gln<br>                      515                      520                    525 | 1584 |
| ctg cag ctg gcc acc cag ttt gag aac tgg tat aag aag tat cag aag<br>Leu Gln Leu Ala Thr Gln Phe Glu Asn Trp Tyr Lys Lys Tyr Gln Lys<br>530                      535                    540 | 1632 |
| ccc att att cag agc gag tat gga gca gaa acg att gca ggg ttt cac<br>Pro Ile Ile Gln Ser Glu Tyr Gly Ala Glu Thr Ile Ala Gly Phe His<br>545                      550                      555                    560 | 1680 |
| cag gat cca cct ctg atg ttc act gaa gag tac cag aaa agt ctg cta<br>Gln Asp Pro Pro Leu Met Phe Thr Glu Glu Tyr Gln Lys Ser Leu Leu<br>                          565                      570                    575 | 1728 |
| gag cag tac cat ctg ggt ctg gat caa aaa cgc aga aaa tat gtg gtt<br>Glu Gln Tyr His Leu Gly Leu Asp Gln Lys Arg Arg Lys Tyr Val Val<br>                  580                      585                    590 | 1776 |
| gga gag ctc att tgg aat ttt gcc gat ttc atg act gaa cag tca ccg<br>Gly Glu Leu Ile Trp Asn Phe Ala Asp Phe Met Thr Glu Gln Ser Pro<br>                      595                      600                    605 | 1824 |
| acg aga gtg ctg ggg aat aaa aag ggg atc ttc act cgg cag aga caa<br>Thr Arg Val Leu Gly Asn Lys Lys Gly Ile Phe Thr Arg Gln Arg Gln<br>610                      615                    620 | 1872 |
| cca aaa agt gca gcg ttc ctt ttg cga gag aga tac tgg aag att gcc<br>Pro Lys Ser Ala Ala Phe Leu Leu Arg Glu Arg Tyr Trp Lys Ile Ala<br>625                      630                    635                    640 | 1920 |
| aat gaa acc agg tat ccc cac tca gta gcc aag tca caa tgt ttg gaa<br>Asn Glu Thr Arg Tyr Pro His Ser Val Ala Lys Ser Gln Cys Leu Glu<br>                          645                      650                    655 | 1968 |

```
aac agc ccg ttt act                                    1983
Asn Ser Pro Phe Thr
            660
```

<210> SEQ ID NO 15
<211> LENGTH: 661
<212> TYPE: PRT
<213> ORGANISM: Homo sapiens

<400> SEQUENCE: 15

```
Met Arg Gly Pro Ser Gly Ala Leu Trp Leu Leu Ala Leu Arg Thr
1               5                   10                  15

Val Leu Gly Ser Asp Asp Asp Asp Asp Ala Glu Ala Glu Thr Gly
                20              25                  30

Leu Gln Gly Gly Met Leu Tyr Pro Gln Glu Ser Pro Ser Arg Glu Cys
        35                  40                  45

Lys Glu Leu Asp Gly Leu Trp Ser Phe Arg Ala Asp Phe Ser Asp Asn
50                  55                  60

Arg Arg Arg Gly Phe Glu Glu Gln Trp Tyr Arg Arg Pro Leu Trp Glu
65                  70                  75                  80

Ser Gly Pro Thr Val Asp Met Pro Val Pro Ser Ser Phe Asn Asp Ile
                85                  90                  95

Ser Gln Asp Trp Arg Leu Arg His Phe Val Gly Trp Val Trp Tyr Glu
            100                 105                 110

Arg Glu Val Ile Leu Pro Glu Arg Trp Thr Gln Asp Leu Arg Thr Arg
        115                 120                 125

Val Val Leu Arg Ile Gly Ser Ala His Ser Tyr Ala Ile Val Trp Val
130                 135                 140

Asn Gly Val Asp Thr Leu Glu His Glu Gly Gly Tyr Leu Pro Phe Glu
145                 150                 155                 160

Ala Asp Ile Ser Asn Leu Val Gln Val Gly Pro Leu Pro Ser Arg Leu
                165                 170                 175

Arg Ile Thr Ile Ala Ile Asn Asn Thr Leu Thr Pro Thr Thr Leu Pro
            180                 185                 190

Pro Gly Thr Ile Gln Tyr Leu Thr Asp Thr Ser Lys Tyr Pro Lys Gly
        195                 200                 205

Tyr Phe Val Gln Asn Thr Tyr Phe Asp Phe Phe Asn Tyr Ala Gly Leu
210                 215                 220

Gln Arg Ser Val Leu Leu Tyr Thr Thr Pro Thr Thr Tyr Ile Asp Asp
225                 230                 235                 240

Ile Thr Val Thr Thr Ser Val Glu Gln Asp Ser Gly Leu Val Asn Tyr
                245                 250                 255

Gln Ile Ser Val Lys Gly Ser Asn Leu Phe Lys Leu Glu Val Arg Leu
            260                 265                 270

Leu Asp Ala Glu Asn Lys Val Val Ala Asn Gly Thr Gly Thr Gln Gly
        275                 280                 285

Gln Leu Lys Val Pro Gly Val Ser Leu Trp Trp Pro Tyr Leu Met His
290                 295                 300

Glu Arg Pro Ala Tyr Leu Tyr Ser Leu Glu Val Gln Leu Thr Ala Gln
305                 310                 315                 320

Thr Ser Leu Gly Pro Val Ser Asp Phe Tyr Thr Leu Pro Val Gly Ile
                325                 330                 335

Arg Thr Val Ala Val Thr Lys Ser Gln Phe Leu Ile Asn Gly Lys Pro
            340                 345                 350

Phe Tyr Phe His Gly Val Asn Lys His Glu Asp Ala Asp Ile Arg Gly
```

```
                355                 360                 365
Lys Gly Phe Asp Trp Pro Leu Leu Val Lys Asp Phe Asn Leu Leu Arg
    370                 375                 380

Trp Leu Gly Ala Asn Ala Phe Arg Thr Ser His Tyr Pro Tyr Ala Glu
385                 390                 395                 400

Glu Val Met Gln Met Cys Asp Arg Tyr Gly Ile Val Val Ile Asp Glu
                405                 410                 415

Cys Pro Gly Val Gly Leu Ala Leu Pro Gln Phe Phe Asn Asn Val Ser
            420                 425                 430

Leu His His His Met Gln Val Met Glu Glu Val Val Arg Arg Asp Lys
        435                 440                 445

Asn His Pro Ala Val Val Met Trp Ser Val Ala Asn Glu Pro Ala Ser
    450                 455                 460

His Leu Glu Ser Ala Gly Tyr Tyr Leu Lys Met Val Ile Ala His Thr
465                 470                 475                 480

Lys Ser Leu Asp Pro Ser Arg Pro Val Thr Phe Val Ser Asn Ser Asn
                485                 490                 495

Tyr Ala Ala Asp Lys Gly Ala Pro Tyr Val Asp Val Ile Cys Leu Asn
            500                 505                 510

Ser Tyr Tyr Ser Trp Tyr His Asp Tyr Gly His Leu Glu Leu Ile Gln
        515                 520                 525

Leu Gln Leu Ala Thr Gln Phe Glu Asn Trp Tyr Lys Lys Tyr Gln Lys
    530                 535                 540

Pro Ile Ile Gln Ser Glu Tyr Gly Ala Glu Thr Ile Ala Gly Phe His
545                 550                 555                 560

Gln Asp Pro Pro Leu Met Phe Thr Glu Glu Tyr Gln Lys Ser Leu Leu
                565                 570                 575

Glu Gln Tyr His Leu Gly Leu Asp Gln Lys Arg Arg Lys Tyr Val Val
            580                 585                 590

Gly Glu Leu Ile Trp Asn Phe Ala Asp Phe Met Thr Glu Gln Ser Pro
        595                 600                 605

Thr Arg Val Leu Gly Asn Lys Lys Gly Ile Phe Thr Arg Gln Arg Gln
    610                 615                 620

Pro Lys Ser Ala Ala Phe Leu Leu Arg Glu Arg Tyr Trp Lys Ile Ala
625                 630                 635                 640

Asn Glu Thr Arg Tyr Pro His Ser Val Ala Lys Ser Gln Cys Leu Glu
                645                 650                 655

Asn Ser Pro Phe Thr
            660

<210> SEQ ID NO 16
<211> LENGTH: 1989
<212> TYPE: DNA
<213> ORGANISM: Homo sapiens
<220> FEATURE:
<221> NAME/KEY: CDS
<222> LOCATION: (1)..(1989)

<400> SEQUENCE: 16 atg cgg ggt ccg agc ggg gct ctg tgg ctg ctc ctg gct ctg cgc acc      48
Met Arg Gly Pro Ser Gly Ala Leu Trp Leu Leu Leu Ala Leu Arg Thr
1               5                   10                  15 gtg ctc gga tca gat gat gat gat gat gat gat gcc gag gca gaa         96
Val Leu Gly Ser Asp Asp Asp Asp Asp Asp Asp Ala Glu Ala Glu
            20                  25                  30 acc ggt ctg cag ggc ggg atg ctg tac ccc cag gag agc ccg tcg cgg    144
Thr Gly Leu Gln Gly Gly Met Leu Tyr Pro Gln Glu Ser Pro Ser Arg
```

-continued

```
                        35                      40                          45
gag  tgc  aag  gag  ctg  gac  ggc  ctc  tgg  agc  ttc  cgc  gcc  gac  ttc  tct        192
Glu  Cys  Lys  Glu  Leu  Asp  Gly  Leu  Trp  Ser  Phe  Arg  Ala  Asp  Phe  Ser
          50                       55                       60 gac  aac  cga  cgc  cgg  ggc  ttc  gag  gag  cag  tgg  tac  cgg  cgg  ccg  ctg        240
Asp  Asn  Arg  Arg  Arg  Gly  Phe  Glu  Glu  Gln  Trp  Tyr  Arg  Arg  Pro  Leu
 65                       70                       75                       80 tgg  gag  tca  ggc  ccc  acc  gtg  gac  atg  cca  gtt  ccc  tcc  agc  ttc  aat        288
Trp  Glu  Ser  Gly  Pro  Thr  Val  Asp  Met  Pro  Val  Pro  Ser  Ser  Phe  Asn
                    85                       90                       95 gac  atc  agc  cag  gac  tgg  cgt  ctg  cgg  cat  ttt  gtc  ggc  tgg  gtg  tgg        336
Asp  Ile  Ser  Gln  Asp  Trp  Arg  Leu  Arg  His  Phe  Val  Gly  Trp  Val  Trp
          100                      105                      110 tac  gaa  cgg  gag  gtg  atc  ctg  ccg  gag  cga  tgg  acc  cag  gac  ctg  cgc        384
Tyr  Glu  Arg  Glu  Val  Ile  Leu  Pro  Glu  Arg  Trp  Thr  Gln  Asp  Leu  Arg
                    115                      120                      125 aca  aga  gtg  gtg  ctg  agg  att  ggc  agt  gcc  cat  tcc  tat  gcc  atc  gtg        432
Thr  Arg  Val  Val  Leu  Arg  Ile  Gly  Ser  Ala  His  Ser  Tyr  Ala  Ile  Val
          130                      135                      140 tgg  gtg  aat  ggg  gtc  gac  acg  cta  gag  cat  gag  ggg  ggc  tac  ctc  ccc        480
Trp  Val  Asn  Gly  Val  Asp  Thr  Leu  Glu  His  Glu  Gly  Gly  Tyr  Leu  Pro
145                      150                      155                      160 ttc  gag  gcc  gac  atc  agc  aac  ctg  gtc  cag  gtg  ggg  ccc  ctg  ccc  tcc        528
Phe  Glu  Ala  Asp  Ile  Ser  Asn  Leu  Val  Gln  Val  Gly  Pro  Leu  Pro  Ser
                    165                      170                      175 cgg  ctc  cga  atc  act  atc  gcc  atc  aac  aac  aca  ctc  acc  ccc  acc  acc        576
Arg  Leu  Arg  Ile  Thr  Ile  Ala  Ile  Asn  Asn  Thr  Leu  Thr  Pro  Thr  Thr
          180                      185                      190 ctg  cca  cca  ggg  acc  atc  caa  tac  ctg  act  gac  acc  tcc  aag  tat  ccc        624
Leu  Pro  Pro  Gly  Thr  Ile  Gln  Tyr  Leu  Thr  Asp  Thr  Ser  Lys  Tyr  Pro
                    195                      200                      205 aag  ggt  tac  ttt  gtc  cag  aac  aca  tat  ttt  gac  ttt  ttc  aac  tac  gct        672
Lys  Gly  Tyr  Phe  Val  Gln  Asn  Thr  Tyr  Phe  Asp  Phe  Phe  Asn  Tyr  Ala
          210                      215                      220 gga  ctg  cag  cgg  tct  gta  ctt  ctg  tac  acg  aca  ccc  acc  acc  tac  atc        720
Gly  Leu  Gln  Arg  Ser  Val  Leu  Leu  Tyr  Thr  Thr  Pro  Thr  Thr  Tyr  Ile
225                      230                      235                      240 gat  gac  atc  acc  gtc  acc  acc  agc  gtg  gag  caa  gac  agt  ggg  ctg  gtg        768
Asp  Asp  Ile  Thr  Val  Thr  Thr  Ser  Val  Glu  Gln  Asp  Ser  Gly  Leu  Val
                    245                      250                      255 aat  tac  cag  atc  tct  gtc  aag  ggc  agt  aac  ctg  ttc  aag  ttg  gaa  gtg        816
Asn  Tyr  Gln  Ile  Ser  Val  Lys  Gly  Ser  Asn  Leu  Phe  Lys  Leu  Glu  Val
          260                      265                      270 cgt  ctt  ttg  gat  gca  gaa  aac  aaa  gtc  gtg  gcg  aat  ggg  act  ggg  acc        864
Arg  Leu  Leu  Asp  Ala  Glu  Asn  Lys  Val  Val  Ala  Asn  Gly  Thr  Gly  Thr
                    275                      280                      285 cag  ggc  caa  ctt  aag  gtg  cca  ggt  gtc  agc  ctc  tgg  tgg  ccg  tac  ctg        912
Gln  Gly  Gln  Leu  Lys  Val  Pro  Gly  Val  Ser  Leu  Trp  Trp  Pro  Tyr  Leu
          290                      295                      300 atg  cac  gaa  cgc  cct  gcc  tat  ctg  tat  tca  ttg  gag  gtg  cag  ctg  act        960
Met  His  Glu  Arg  Pro  Ala  Tyr  Leu  Tyr  Ser  Leu  Glu  Val  Gln  Leu  Thr
305                      310                      315                      320 gca  cag  acg  tca  ctg  ggg  cct  gtg  tct  gac  ttc  tac  aca  ctc  cct  gtg       1008
Ala  Gln  Thr  Ser  Leu  Gly  Pro  Val  Ser  Asp  Phe  Tyr  Thr  Leu  Pro  Val
                    325                      330                      335 ggg  atc  cgc  act  gtg  gct  gtc  acc  aag  agc  cag  ttc  ctc  atc  aat  ggg       1056
Gly  Ile  Arg  Thr  Val  Ala  Val  Thr  Lys  Ser  Gln  Phe  Leu  Ile  Asn  Gly
          340                      345                      350 aaa  cct  ttc  tat  ttc  cac  ggt  gtc  aac  aag  cat  gag  gat  gcg  gac  atc       1104
Lys  Pro  Phe  Tyr  Phe  His  Gly  Val  Asn  Lys  His  Glu  Asp  Ala  Asp  Ile
```

-continued

```
              355                 360                 365
cga ggg aag ggc ttc gac tgg ccg ctg ctg gtg aag gac ttc aac ctg      1152
Arg Gly Lys Gly Phe Asp Trp Pro Leu Leu Val Lys Asp Phe Asn Leu
370                 375                 380 ctt cgc tgg ctt ggt gcc aac gct ttc cgt acc agc cac tac ccc tat      1200
Leu Arg Trp Leu Gly Ala Asn Ala Phe Arg Thr Ser His Tyr Pro Tyr
385                 390                 395                 400 gca gag gaa gtg atg cag atg tgt gac cgc tat ggg att gtg gtc atc      1248
Ala Glu Glu Val Met Gln Met Cys Asp Arg Tyr Gly Ile Val Val Ile
            405                 410                 415 gat gag tgt ccc ggc gtg ggc ctg gcg ctg ccg cag ttc ttc aac aac      1296
Asp Glu Cys Pro Gly Val Gly Leu Ala Leu Pro Gln Phe Phe Asn Asn
420                 425                 430 gtt tct ctg cat cac cac atg cag gtg atg gaa gaa gtg gtg cgt agg      1344
Val Ser Leu His His His Met Gln Val Met Glu Glu Val Val Arg Arg
435                 440                 445 gac aag aac cac ccc gcg gtc gtg atg tgg tct gtg gcc aac gag cct      1392
Asp Lys Asn His Pro Ala Val Val Met Trp Ser Val Ala Asn Glu Pro
450                 455                 460 gcg tcc cac cta gaa tct gct ggc tac tac ttg aag atg gtg atc gct      1440
Ala Ser His Leu Glu Ser Ala Gly Tyr Tyr Leu Lys Met Val Ile Ala
465                 470                 475                 480 cac acc aaa tcc ttg gac ccc tcc cgg cct gtg acc ttt gtg agc aac      1488
His Thr Lys Ser Leu Asp Pro Ser Arg Pro Val Thr Phe Val Ser Asn
            485                 490                 495 tct aac tat gca gca gac aag ggg gct ccg tat gtg gat gtg atc tgt      1536
Ser Asn Tyr Ala Ala Asp Lys Gly Ala Pro Tyr Val Asp Val Ile Cys
500                 505                 510 ttg aac agc tac tac tct tgg tat cac gac tac ggg cac ctg gag ttg      1584
Leu Asn Ser Tyr Tyr Ser Trp Tyr His Asp Tyr Gly His Leu Glu Leu
515                 520                 525 att cag ctg cag ctg gcc acc cag ttt gag aac tgg tat aag aag tat      1632
Ile Gln Leu Gln Leu Ala Thr Gln Phe Glu Asn Trp Tyr Lys Lys Tyr
530                 535                 540 cag aag ccc att att cag agc gag tat gga gca gaa acg att gca ggg      1680
Gln Lys Pro Ile Ile Gln Ser Glu Tyr Gly Ala Glu Thr Ile Ala Gly
545                 550                 555                 560 ttt cac cag gat cca cct ctg atg ttc act gaa gag tac cag aaa agt      1728
Phe His Gln Asp Pro Pro Leu Met Phe Thr Glu Glu Tyr Gln Lys Ser
            565                 570                 575 ctg cta gag cag tac cat ctg ggt ctg gat caa aaa cgc aga aaa tat      1776
Leu Leu Glu Gln Tyr His Leu Gly Leu Asp Gln Lys Arg Arg Lys Tyr
580                 585                 590 gtg gtt gga gag ctc att tgg aat ttt gcc gat ttc atg act gaa cag      1824
Val Val Gly Glu Leu Ile Trp Asn Phe Ala Asp Phe Met Thr Glu Gln
595                 600                 605 tca ccg acg aga gtg ctg ggg aat aaa aag ggg atc ttc act cgg cag      1872
Ser Pro Thr Arg Val Leu Gly Asn Lys Lys Gly Ile Phe Thr Arg Gln
610                 615                 620 aga caa cca aaa agt gca gcg ttc ctt ttg cga gag aga tac tgg aag      1920
Arg Gln Pro Lys Ser Ala Ala Phe Leu Leu Arg Glu Arg Tyr Trp Lys
625                 630                 635                 640 att gcc aat gaa acc agg tat ccc cac tca gta gcc aag tca caa tgt      1968
Ile Ala Asn Glu Thr Arg Tyr Pro His Ser Val Ala Lys Ser Gln Cys
            645                 650                 655 ttg gaa aac agc ccg ttt act                                          1989
Leu Glu Asn Ser Pro Phe Thr
660
```

<210> SEQ ID NO 17

<211> LENGTH: 663
<212> TYPE: PRT
<213> ORGANISM: Homo sapiens

<400> SEQUENCE: 17

```
Met Arg Gly Pro Ser Gly Ala Leu Trp Leu Leu Leu Ala Leu Arg Thr
1               5                   10                  15

Val Leu Gly Ser Asp Asp Asp Asp Asp Asp Ala Glu Ala Glu
            20                  25                  30

Thr Gly Leu Gln Gly Gly Met Leu Tyr Pro Gln Ser Pro Ser Arg
        35                  40                  45

Glu Cys Lys Glu Leu Asp Gly Leu Trp Ser Phe Arg Ala Asp Phe Ser
    50                  55                  60

Asp Asn Arg Arg Arg Gly Phe Glu Glu Gln Trp Tyr Arg Arg Pro Leu
65                  70                  75                  80

Trp Glu Ser Gly Pro Thr Val Asp Met Pro Val Pro Ser Ser Phe Asn
                85                  90                  95

Asp Ile Ser Gln Asp Trp Arg Leu Arg His Phe Val Gly Trp Val Trp
            100                 105                 110

Tyr Glu Arg Glu Val Ile Leu Pro Glu Arg Trp Thr Gln Asp Leu Arg
        115                 120                 125

Thr Arg Val Val Leu Arg Ile Gly Ser Ala His Ser Tyr Ala Ile Val
130                 135                 140

Trp Val Asn Gly Val Asp Thr Leu Glu His Glu Gly Gly Tyr Leu Pro
145                 150                 155                 160

Phe Glu Ala Asp Ile Ser Asn Leu Val Gln Val Gly Pro Leu Pro Ser
                165                 170                 175

Arg Leu Arg Ile Thr Ile Ala Ile Asn Asn Thr Leu Thr Pro Thr Thr
            180                 185                 190

Leu Pro Pro Gly Thr Ile Gln Tyr Leu Thr Asp Thr Ser Lys Tyr Pro
        195                 200                 205

Lys Gly Tyr Phe Val Gln Asn Thr Tyr Phe Asp Phe Phe Asn Tyr Ala
210                 215                 220

Gly Leu Gln Arg Ser Val Leu Leu Tyr Thr Thr Pro Thr Thr Tyr Ile
225                 230                 235                 240

Asp Asp Ile Thr Val Thr Thr Ser Val Glu Gln Asp Ser Gly Leu Val
                245                 250                 255

Asn Tyr Gln Ile Ser Val Lys Gly Ser Asn Leu Phe Lys Leu Glu Val
            260                 265                 270

Arg Leu Leu Asp Ala Glu Asn Lys Val Val Ala Asn Gly Thr Gly Thr
        275                 280                 285

Gln Gly Gln Leu Lys Val Pro Gly Val Ser Leu Trp Trp Pro Tyr Leu
290                 295                 300

Met His Glu Arg Pro Ala Tyr Leu Tyr Ser Leu Glu Val Gln Leu Thr
305                 310                 315                 320

Ala Gln Thr Ser Leu Gly Pro Val Ser Asp Phe Tyr Thr Leu Pro Val
                325                 330                 335

Gly Ile Arg Thr Val Ala Val Thr Lys Ser Gln Phe Leu Ile Asn Gly
            340                 345                 350

Lys Pro Phe Tyr Phe His Gly Val Asn Lys His Glu Asp Ala Asp Ile
        355                 360                 365

Arg Gly Lys Gly Phe Asp Trp Pro Leu Leu Val Lys Asp Phe Asn Leu
370                 375                 380

Leu Arg Trp Leu Gly Ala Asn Ala Phe Arg Thr Ser His Tyr Pro Tyr
385                 390                 395                 400
```

```
Ala Glu Glu Val Met Gln Met Cys Asp Arg Tyr Gly Ile Val Ile
            405                 410                 415

Asp Glu Cys Pro Gly Val Gly Leu Ala Leu Pro Gln Phe Phe Asn Asn
            420                 425                 430

Val Ser Leu His His Met Gln Val Met Glu Glu Val Arg Arg
            435                 440                 445

Asp Lys Asn His Pro Ala Val Val Met Trp Ser Val Ala Asn Glu Pro
450                 455                 460

Ala Ser His Leu Glu Ser Ala Gly Tyr Tyr Leu Lys Met Val Ile Ala
465                 470                 475                 480

His Thr Lys Ser Leu Asp Pro Ser Arg Pro Val Thr Phe Val Ser Asn
                485                 490                 495

Ser Asn Tyr Ala Ala Asp Lys Gly Ala Pro Tyr Val Asp Val Ile Cys
                500                 505                 510

Leu Asn Ser Tyr Tyr Ser Trp Tyr His Asp Tyr Gly His Leu Glu Leu
                515                 520                 525

Ile Gln Leu Gln Leu Ala Thr Gln Phe Glu Asn Trp Tyr Lys Lys Tyr
530                 535                 540

Gln Lys Pro Ile Ile Gln Ser Glu Tyr Gly Ala Glu Thr Ile Ala Gly
545                 550                 555                 560

Phe His Gln Asp Pro Pro Leu Met Phe Thr Glu Glu Tyr Gln Lys Ser
                565                 570                 575

Leu Leu Glu Gln Tyr His Leu Gly Leu Asp Gln Lys Arg Arg Lys Tyr
                580                 585                 590

Val Val Gly Glu Leu Ile Trp Asn Phe Ala Asp Phe Met Thr Glu Gln
                595                 600                 605

Ser Pro Thr Arg Val Leu Gly Asn Lys Lys Gly Ile Phe Thr Arg Gln
            610                 615                 620

Arg Gln Pro Lys Ser Ala Ala Phe Leu Leu Arg Glu Arg Tyr Trp Lys
625                 630                 635                 640

Ile Ala Asn Glu Thr Arg Tyr Pro His Ser Val Ala Lys Ser Gln Cys
                645                 650                 655

Leu Glu Asn Ser Pro Phe Thr
            660

<210> SEQ ID NO 18
<211> LENGTH: 52
<212> TYPE: DNA
<213> ORGANISM: Artificial
<220> FEATURE:
<223> OTHER INFORMATION: forward primer. Nt1-5: random synthetic
      sequence. Nt6-52: part of sequence encoding p97 signal.

<400> SEQUENCE: 18
gtaccgaatt caccgccatg cggggtccga gcggggctct gtggctgctc ct          52

<210> SEQ ID NO 19
<211> LENGTH: 51
<212> TYPE: DNA
<213> ORGANISM: Artificial
<220> FEATURE:
<223> OTHER INFORMATION: reverse primer. Nt1-6: random synthetic
      sequence. Nt 7-52: part of sequence encoding p97 signal.

<400> SEQUENCE: 19
gtaccgggat ccgagcacgg tgcgcagagc caggagcagc cacagagccc c           51
```

ENHANCING THE EFFECT OF THERAPEUTIC PROTEINS ON THE CENTRAL NERVOUS SYSTEM

PARENT CASE TEXT

This application is a divisional of U.S. application Ser. No. 11/614,970 filed Dec. 21, 2006, abandoned, which is a continuation in part of U.S. application Ser. No. 11/245,424 filed on Oct. 7, 2005, abandoned, which is a continuation in part of U.S. application Ser. No. 10/864,758, filed Jun. 10, 2004, now U.S. Pat. 7,863,238. All of the above are incorporated herein by reference in their entirety.

GOVERNMENT SUPPORT CLAUSE

This work was supported by the National Institutes of Health grant number GM34182, and International Morquio Organization. U.S. Government has certain rights in this invention.

BACKGROUND OF THE INVENTION

1. Field of the Invention

The present invention relates to endowing therapeutic protein agents with increased in vivo stability and effectiveness on the central nervous system (CNS). More specifically, the present invention relates to endowing β-glucuronidase protein (GUS) with improved stability in the blood and enhanced ability to affect the CNS, in a therapeutic capacity by attaching a short peptide of acidic amino acids to the N-terminus of the protein.

2. Description of the Related Art

Lysosomal storage diseases (LSDs) are a class of forty rare genetic disorders, each of which is caused by a deficiency in a specific lysosomal enzyme. As a consequence of the progressive accumulation of unmetabolized macromolecules in the lysosomes of cells in various tissues, the disease manifestations worsen over time.[1] Individuals afflicted with an LSD can suffer from mild to severe physical and/or neurological abnormalities or can die at an early age. A therapeutic paradigm for the treatment of LSDs was established with the success of enzyme-replacement therapy (ERT) for the treatment of Gaucher disease.[2,3] In the case of Gaucher disease, delivery of the enzyme to the affected cells was achieved by modifying the N-linked carbohydrate on the enzyme. This exposed core mannose residues,[4,5] enabling the enzyme to bind to the MR, which is highly abundant on cells of the reticuloendothelial system.[6,7] These findings led to clinical management of Gaucher disease by ERT.[8] Over 3,500 patients have been treated with dramatic clinical results.[9]

Meanwhile there is a problem that pharmaceutical preparations of physiologically active proteins like enzymes and peptide hormones are generally made unstable when they are administered to the body, and thus undergo relatively rapid inactivation by, e.g., enzymatic degradation. For pharmaceutical preparations of a physiologically active protein, a method for increasing the stability of the physiologically active protein in the body is known which is based on coupling the proteins to polyethylene glycol.[10]

Sly's syndrome is an autosomal recessive, genetic lysosomal storage disease caused by an anomaly in the gene for a lysosomal enzyme, β-glucuronidase (hereinafter referred to as GUS)[11](6), and is classified as type VII mucopolysaccharidosis (hereinafter referred to as MPS VII). In lysosomes, GUS acts as an exoglycosidase to remove glucuronic acid residues from the non-reducing termini of GAGs (glycosaminoglycans), such as dermatan sulfate (DS), heparan sulfate (HS), and chondroitin sulfate (CS). In the absence of GUS, GAGs are only partially degraded and accumulate in lysosomes of a variety of tissues. Progressive accumulation of undegraded GAGs in lysosomes affects the spleen, liver, kidney, cornea, brain, heart valves, and the skeletal system, leading to facial dysmorphism, growth retardation, systemic bone dysplasia, deafness, mental retardation, and shortened lifespan.

No effective remedy is currently available for MPS VII. Enzyme replacement therapy (ERT) has been considered to be the potential remedy for MPS VII. Considering its rapid inactivation in the body, however, native GUS is not expected to give any satisfactory effect.

The challenge is to improve joint and brain-related pathology since most of the enzyme-based drugs are delivered to major visceral organs like liver and spleen and only a small amount of enzyme is delivered to bone and brain. Many lysosomal enzymes have a short half-life when injected into the bloodstream because of rapid clearance in the liver by carbohydrate-recognizing receptors, particularly the mannose receptor that is highly abundant on Kupffer cells.[12] Although a part of the enzyme reaches the bone marrow, there is no way to guarantee that the enzyme will reach the brain since the blood brain barrier presents a formidable obstacle. As a result, current ERT does not work efficiently on the bone and brain lesions.

The inventors have sought to address the problem of stability of therapeutic proteins in vivo and the inability of some proteins to effectively cross the blood brain barrier. The inventors have previously disclosed the use of short peptides of acidic amino acids to target proteins to bone tissue for use in Enzyme Replacement Therapy (ERT).[13] The inventors have also disclosed the use of short peptides of acidic amino acids to improve stability of physiological active proteins in the blood.

The addition of 4-15 acidic amino acids to GUS results in an increase in molecular weight which generally, would not be expected to increase functional activity of proteins to the CNS. In fact, higher molecular weigh molecules are more effectively excluded from the brain by an ineffectual crossing the blood brain barrier. Similarly, an increase in the hydrophilic nature of a molecule is also thought to exclude molecules at the blood brain barrier. The inventors have made the surprising discovery that despite causing an apparent increase in molecular weight and increase in hydrophilic nature, the addition of an acid amino acid leader to GUS has allowed enhanced therapeutic benefits on the brain.

SUMMARY OF THE INVENTION

An object of the present invention is a method to increase in vivo stability of a physiologically active peptide or protein by the addition of a short acidic amino acid leader, and thereby increase its therapeutic effects on the CNS for treatment of CNS related disease.

Previously, the inventors made the unexpected discovery that N-acetylgalactosamine-6-sulfate sulfatase (GALNS), tissue-nonspecific alkaline phosphatase (TNSALP) and GUS with a short amino acidic peptide (AAA) attached to the N-terminus increased targeting and deposition of these enzymes to bone. They further discovered that GALNS and GUS, with this short acidic amino acidic peptide attached possessed improved in vivo stability in the blood. The inventors have now further discovered that AAA-GUS possessed improved functional activity to tissues of the CNS, when administered to a patient with MPS VII.

The addition of a short amino acidic peptide attached to the N-terminus of GUS or other physiology active proteins possessing CNS therapeutic activity will endow these molecules with enhanced therapeutic benefits for the treatment for patients with CNS disorders. Compared with native physiologically active GUS, the present invention described above provides a physiologically active fusion protein with increased stability in the blood and increased therapeutic effects on the brain when administered to a patient with MPS VII.

Therefore, an object of this invention is 1) a polypeptide therapeutic agent with increased benefits for the CNS, 2) a method of increasing beneficial effects on the CNS, of a protein or polypeptide possessing CNS therapeutic activity, by attaching a 4-15 acid amino acid leader through chemical modification or genetic engineering of a fusion protein and 3) a method of treatment for patients suffering from CNS related diseases with the afore mentioned preparation.

DETAILED DESCRIPTION OF THE INVENTION

Figure 1:
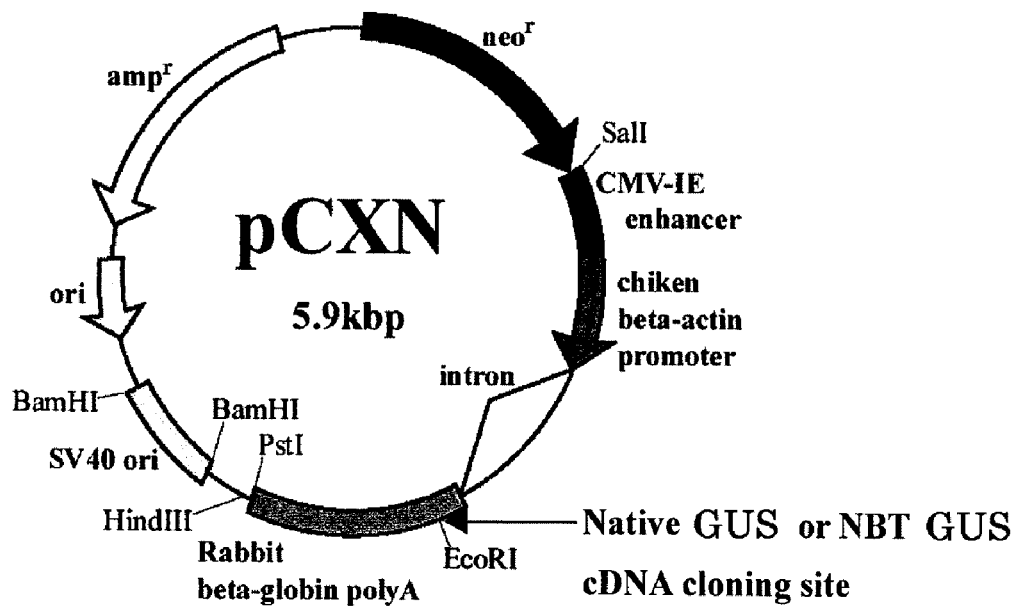
FIG. 1: is a schematic diagram illustrating pCXN vector and the cloning site in the vector for the cDNA encoding native GUS or the GUS fusion protein

Mucopolysaccharidoses (MPS) are a group of lysosomal storage disorders (LSDs) caused by deficiency of the lysosomal enzymes needed to degrade glycosaminoglycans (GAGs).[14] In MPS, the undegraded GAGs are stored in lysosomes and/or secreted into the blood stream[15,16], and excreted in urine. MPS involve the deficiency of one of 11 enzymes needed for the stepwise degradation of DS, HS, KS, and/or CS.

ERT is an established means of treating MPS. However, improving bone and brain pathology is still an unmet challenge because only a small fraction of enzyme is delivered to bone and brain. Most of the enzyme-based drugs are delivered to major visceral organs like liver and spleen. Although some of the enzyme reaches bone marrow, only small amounts of the enzyme go to bone or brain. The blood brain barrier provides a formidable obstacle for enzymes to reach brain. Therefore, the improvement of bone and brain lesions is quite limited, even after long-term treatment with ERT. We have tested an acidic oligopeptide-based targeting system for delivery of enzymes to tissues in murine MPS IVA and VII models. This strategy is based on tagging a short peptide consisting of acidic amino acids (AAA) to the mature enzyme. The AAA-tagged enzyme had five to ten times prolonged blood clearance compared with the untagged enzymes. The tagged enzyme was delivered effectively to bone, bone marrow, and brain in MPS VII mice and was more effective in reversing the storage pathology than the untagged enzyme.

Others have shown therapeutic responses in brain of mouse models MPS VII, aspartylglycosaminuria and β-mannosidosis when higher doses and longer treatment with enzyme is made possible.[17,18,19] These results indicate that when therapeutic enzyme is administered over a sufficient period, at doses higher than those used in conventional ERT trials such a therapeutic dose has a beneficial effect in an adult mouse. The present invention allows such beneficial effects to be achieved with the administration of less therapeutic enzyme.

Therefore, the present invention discloses 1) an enzyme with therapeutic benefits for the CNS whereby said benefits are enhanced by the attachment of an AAA sequence, 2) a method of attaching an acidic amino acid sequence to a therapeutic enzyme with benefits for the CNS so as to allow said benefits to be delivered to the CNS under conditions which would otherwise be ineffectual, 3) a method of treating a patient with an CNS related disease using the aforementioned AAA-therapeutic enzyme.

The inventors have previous disclosed AAA-GALNS which is hereby incorporated by reference.[20] This reference discloses a fusion protein for the treatment of disease, and a method of increasing the stability of a therapeutic protein in blood and transfer of said protein to bone. More specifically the therapeutic protein is GALNS and the disease is Morquio disease.

The inventors have also previously disclosed an AAA-GUS, described in detail bellow, and herein incorporated by reference.[21] This reference discloses a fusion protein AAA-GUS for the treatment of disease with improved in vivo stability and a method for treating a patient with MPS VII.

The term "polypeptide therapeutic agent" refereed to in the present invention means any polypeptide, oligopeptide or protein which will benefit a patient suffering from disease when administered to the patient.

The term "acidic amino acid" or "AAA" referred to the present invention means glutamic acid or aspartic acid. As the employment of these acidic amino acids in the present invention is for the purpose of constructing an acidic short peptide, they may be used in any arbitrary combination including a simple use of one or the other of them alone for construction of such a short peptide. The number of the acidic amino acids forming a short peptide is preferably 4-15, more preferably 4-12, and still more preferably 4-8.

A short peptide consisting of acidic amino acids may be directly attached to the N-terminus of physiologically active human GUS via a peptide bond or like, or, instead, it may be attached via a linker peptide.

In the present invention "a linker peptide" is not an indispensable component, for it is usable only for convenience in attaching a short peptide consisting of acidic amino acids to N-terminus of physiologically active GUS. Where it is used, a linker peptide may be a short peptide consisting e.g., preferably of 15 or less, more preferably of 10 or less, and still more preferably of 6 or less amino acids. Such a linker that consists of a single amino acid molecule and linking between the acidic short peptide and physiologically active GUS via peptide bonds is also included in the definition of a linker peptide. A linker peptide may be made of any one or more amino acids desired.

In the present invention, though there is no specific limitation as to the method for attaching an acidic short peptide to physiologically active GUS, it is of advantage, e.g., to form and use a transformant cell expressing the fusion protein consisting of the short peptide and physiologically active GUS.

In the present invention "attachment" in reference to acidic amino acids or AAA and therapeutic proteins or peptides or enzymes refers to creation of a covalent bond either through the creation of a fusion protein or through the use of chemical agents or manipulation to achieve the same result.

A fusion protein of the present invention may include a non-acidic amino acid or a sequence of several (e.g., 3) non-acidic amino acids at N-terminus of the short peptide consisting of acidic amino acids.

A fusion protein of the present invention may be formulated into a pharmaceutical composition containing the fusion protein dissolved or dispersed in a pharmaceutically acceptable carrier well known to those skilled in the art, for parenteral administration by e.g., intravenous, subcutaneous, or intramuscular injection or by intravenous drip infusion.

For pharmaceutical compositions for parenteral administration; any conventional additives may be used such as excipients, binders, disintegrants, dispersing agent, lubricants, diluents, absorption enhancers, buffering agents, surfactants, solubilizing agents, preservatives, emulsifiers, isotonizers, stabilizers, solubilizers for injection, pH adjusting agents, etc.

A fusion protein of the present invention may be used advantageously in place of the conventional native enzyme protein in a substitution therapy for the treatment of MPS VII. In the treatment, the fusion protein may be administered intravenously, subcutaneously, or intramuscularly. Doses and frequencies of administration are to be determined by the physician in charge in accordance with the condition of his or her patient.

Preferred embodiments of the invention are described in the following examples. Other embodiments within the scope of the claims herein will be apparent to one skilled in the art from consideration of the specification or practice of the invention as disclosed herein. It is intended that the specification, together with the examples, be considered exemplary only, with the scope and spirit of the invention being indicated by the claims, which follow the examples.

EXAMPLE 1

Method for Construction of Expression Vectors

Figure 2:
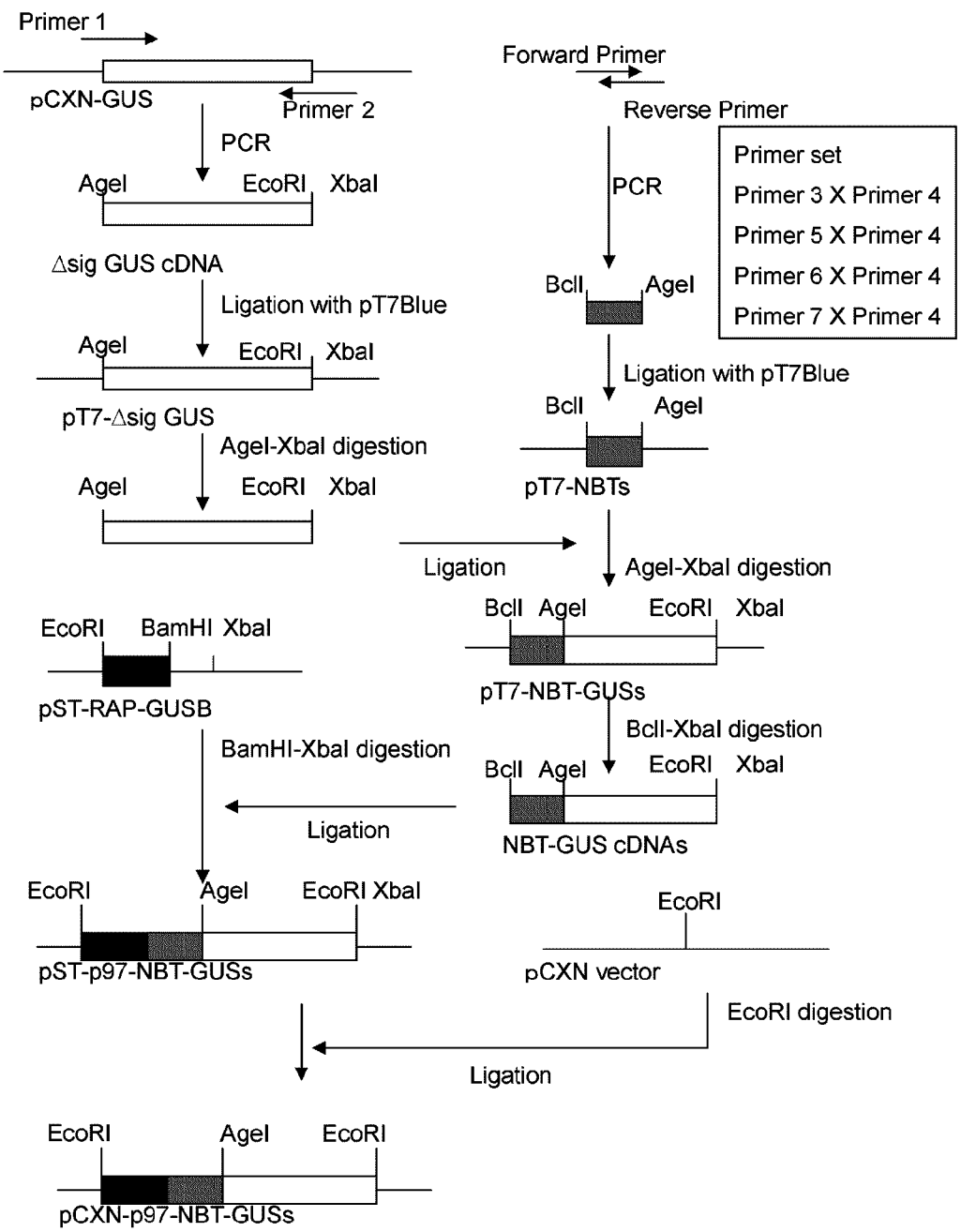
FIG. 2: illustrates the steps for the construction of an expression vector for the production of the GUS and GUS fusion protein.

Vector pCXN had been constructed in accordance with a literature (7) and was offered to us by Prof. Miyazaki at Osaka University. An expression vector for native human GUS, pCXN-GUS, was constructed by using human GUS cDNA that had been reported by Oshima et al. (8) (Accession No. of GenBank for the Amino acid and cDNA sequence of Human GUS is BC014142.). An expression vector for human GUS to the N-terminus of which is attached (via a linker peptide) a short peptide (N-terminal bone tag: NBT) consisting of acidic amino acids (NBT-GUS), was constructed starting with pCXN-GUS in the following manner. FIGS. 1 and 2 schematically illustrate the process for construction.

Using pCXN-GUS as a template, PCR was carried out using LA-Taq (Takara) to amplify Δsig GUS cDNA (the sequence, nt 67-1956, left behind after removal of the sequence of nt 1-66 corresponding to a secretion signal, from the ORF region of the sequence set forth as SEQ ID NO:1) (for human GUS without signal sequence, see SEQ ID NO:2), to the 5'-terminus of which is attached an AgeI cleavage sequence. The PCR was carried out according to the instruction for use of LA-Taq, i.e., through the cycles consisting of 30 seconds at 94° C., (30 seconds at 94° C., 30 seconds at 60° C., and 2 minutes at 72° C.)×25, and then 3 minutes at 72° C., with primer 1 (SEQ ID NO:3), and primer 2 (SEQ ID NO:4). The cDNA thus amplified was inserted into pT7Blue vector (Novagen) to construct pT7-Δsig GUS.

The N-terminal bone tag (NBT) cDNA to be attached to the 5'-terminus then was constructed by PCR using LA-Taq (Takara). Briefly, primer 3 (SEQ ID NO:5) and primer 4 (SEQ ID NO:6) were used for the construction of NBT-E6 cDNA, primer 5 (SEQ ID NO:7) and primer 4 (SEQ ID NO:6) for the construction of NBT-E8 cDNA, primer 6 (SEQ ID NO:8) and primer 4 (SEQ ID NO:6) for the construction of NBT-D6 cDNA, and primer 7 (SEQ ID NO:9) and primer 4 (SEQ ID NO:6) for the construction of NBT-D8 cDNA. In the names of the NBT cDNAs, "E6" or "E8" indicate that the NBT is made up of 6 or 8 serially connected glutamic acid residues, respectively. Likewise, "D6" or "D8" indicates that the NBT is made up of 6 or 8 connected aspartic acid residues, respectively.

Employing each pair of the above primers, which contained a portion complementary to each other, PCR was carried out through the cycles consisting of 30 seconds at 94° C., (30 seconds at 94° C., 30 seconds at 60° C., 30 seconds at 72° C.)×20 minutes, and then one minute at 72° C. The thus amplified DNA fragments were inserted into pT7Blue vector (Novagen) to construct pT7-NBTs.

A human GUS cDNA recovered as a fragment of pT7 pT7-Δsig GUS cleaved with AgeI and XbaI was inserted into the AgeI-XbaI site of pT7-NBTs to construct pT7-NBT-GUSs. Then each of pT7-NBT-GUSs was cleaved with BclI, blunt-ended with T4 DNA polymerase, and cleaved with XbaI to recover NBT-GUS cDNAs.

pST-RAP-GUSB (a vector comprising the p97 signal sequence, provided by Tomatsu at Saint Louis University) was cleaved with BamHI and XbaI, into which then was inserted the NBT-GUS cDNAs recovered above to construct pST-p97-NBT-GUSs.

pST-p97-NBT-GUSs were cleaved with EcoRI to recover respective p97-NBT-GUS cDNAs, each of which then was inserted into the EcoRI site of pCXN to construct a NBT-GUS expression vector, pCXN-p97-NBT-GUS. The DNA sequence of the expression vectors' region corresponding to the p97-NBT-D6-GUS, p97-NBT-D8-GUS, p97-NBT-E6-GUS and p97-NBT-E8-GUS cDNAs are shown in the Sequence Listing (SEQ ID NO:10, SEQ ID NO:12, SEQ ID NO:14, SEQ ID NO:16,) along with their corresponding amino acid sequences (SEQ ID NO:11, SEQ ID NO:13, SEQ ID NO:15, SEQ ID NO:17), respectively.

SEQ ID NO:10 shows part of the sequence containing the NBT-E6-GUS cDNA of pCXN-p97-NBT-E6-GUS. Its nt 1-57 encode the p97 signal sequence, nt 61-78 a poly Glu, nt 79-96 a linker sequence, and nt 97-1983 GUS without the signal sequence.

SEQ ID NO:11 shows the NBT-E6-GUS amino acid sequence with the p97 signal sequence. Aa 1-19: p97 signal sequence, aa21-26: poly Glu, aa 27-32: linker sequence, aa 33-661: GUS without signal sequence.

SEQ ID NO:12 shows part of the sequence containing the NBT-E8-GUS cDNA of pCXN-p97-NBT-E8-GUS. Its nt 1-57 encode the p97 signal sequence, nt 61-84 a poly Glu, nt 85-102 a linker sequence, and nt 103-1989 GUS without the signal sequence.

SEQ ID NO:13 shows the NBT-E8-GUS amino acid sequence with attached p97 signal sequence. Aa 1-19: p97 signal sequence, aa 21-28: poly Glu, aa 29-34: linker sequence, aa 35-663: GUS without signal sequence.

SEQ ID NO:14 shows part of the sequence containing the NBT-D6-GUS cDNA of pCXN-p97-NBT-D6-GUS. Its nt 1-57 encode the p97 signal sequence, nt 61-78 a poly Asp, nt 79-96 a linker sequence, and nt 97-1983 GUS without the signal sequence.

SEQ ID NO:15 shows the NBT-D6-GUS amino acid sequence with attached p97 signal sequence. Aa 1-19: p97 signal sequence, aa21-26: poly Asp, aa 27-32: linker sequence, aa 33-661: GUS without signal sequence.

SEQ ID NO:16 shows part of the sequence containing the NBT-D8-GUS cDNA of pCXN-p97-NBT-D8-GUS. Its nt 1-57 encode the p97 signal sequence, nt 61-84 a poly Asp, nt 85-102 a linker sequence, and nt 103-1989 GUS without the signal sequence.

SEQ ID NO:17 shows the NBT-D8-GUS amino acid sequence with attached p97 signal sequence. Aa 1-19: p97 signal sequence, aa 21-28: poly Asp, aa 29-34: linker sequence, aa 35-663: GUS without signal sequence.

The proteins set forth as SEQ ID NO:11, SEQ ID NO:13, SEQ ID NO:15 and SEQ ID NO:17 contain the p97 secretion signal sequence. The signal sequence is removed during secretion process from the cell and the fusion proteins are thus recovered as NBT-GUS in the medium.

p97 is a cell-surface glycoprotein occurring in most human melanomas and its signal sequence consists of 19 amino acids (9). The aforementioned pCXN-p97-NBT-GUSs containing the cDNA encoding this signal sequence may also be constructed by the following method. Briefly, a cDNA containing the p97 signal sequence is synthesized through the process of primers annealing and PCR amplification. LA-Taq is used as an enzyme for PCR. As primers having mutually complementary portions, primer 8 (SEQ ID NO:18) and primer 9 (SEQ ID NO:19) are used. PCR is performed through the cycles of 30 seconds at 94° C., (30 seconds at 94° C., 30 seconds at 60° C., 30 seconds at 72° C.)×20, and one minute at 72° C. The amplified cDNA containing the p97 signal sequence is cleaved with BamHI and EcoRI. Into the pCXN vector, after cleaved with EcoRI, are simultaneously incorporated the aforementioned NBT-GUSs cDNA recovered after the enzyme treatment and cDNA for the p97 signal sequence, giving pCXN-p97-NBT-GUSs.

SEQ ID No:18 is a forward primer, in which nt 1-5 comprise a random synthetic sequence, and nt 6-52 comprise part of the sequence encoding the p97 signal.

SEQ ID No:19 is a reverse primer, in which nt 1-6 comprise a random synthetic sequence, and nt 7-52 comprise part of the sequence encoding the p97 signal.

Establishment of Expression Cells

Nunclon delta-MultiDish 6 Well was inoculated with CHO-K1 cells. After an overnight culture in DMEM/F12/FBS medium [DMEM/F12 medium (Gibco) supplemented with 10% fetal bovine serum (Thermo Trace)], each of the expression vector constructed above was introduced into the cells using Lipofectamine 2000 reagent. For experimental procedures, the instruction manual attached to the Lipofectamine 2000 reagent was followed. After a two-day incubation at 37° C. in 5% $CO_2$, the cells were added to 75-$cm^2$ tissue culture flasks (Iwaki) and incubated until colonies of resistant cells were formed with Genetcin (Gibco) added to the DMEM/F12/FBS medium at the final concentration of 1 mg/mL. After formation of colonies was confirmed under a microscope, cells which exhibited stable expression were cloned by the limiting dilution-culture method. Screening for expression cells were performed by GUS-specific enzyme activity assay of the culture supernatants. Cell lines thus established were subcultured in DMEM/F12/FBS medium supplemented with 0.2 mg/mL Geneticin.

Method for Measurement of GUS-Specific Enzyme Activity

After intravenous administration of native- or NBT-GUS to mice, GUS activity in the blood was determined as follows. Briefly, 12.5 uL of plasma sample from the mice was added to 50 uL of a solution of 10 mM 4-methylumbelliferyl-β-D-glucuronide (Sigma Chemical Co., St. Louis, Mo., cat #M9130) which had been prepared using determination buffer (0.1M sodium acetate buffer pH 4.8), and reaction was allowed for 1 hr at 37° C. Then, 950 uL of stop buffer (1 M Glycine-HCl, pH 10.5) was added and mixed to stop the enzyme reaction. Samples of the reaction mixture were transferred to a fluorometer for measurement with excitation 366 nm/emission 450 nm.

Expression and Purification of Native GUS and GUS Fusion Protein

Native GUS and GUS fusion proteins were produced in overexpressing CHO cells, which were grown to confluency and fed with low-serum medium (Waymouth's MB 752/1 medium, supplemented with 2% FBS/1.2 mM glutamine/1 mM pyruvate) (Gibco) for purification every 24 hr. The media of the culture were pooled, centrifuged at 5,000×g for 20 min at 4° C., and frozen at −20° C. Purification was performed using affinity chromatography (10). Briefly, the conditioned medium from cells overexpressing the Native GUS or a GUS fusion protein was filtered, and NaCl was added to the medium at the final concentration of 0.5 M. The medium was applied to a 5 ml column of Affi-Gel 10 (BioRad) which carried an anti-human GUS monoclonal antibody and had been pre-equilibrated with wash buffer. The column was washed at 36 mL/hour with 20-column volumes of wash buffer. The column was eluted at 36 mL/hour with 50 ml of 10 mM sodium phosphate (pH 5.0) containing 3.5 M $MgCl_2$. Fractions were collected and subjected to GUS activity assay. Fractions containing the enzyme activity were pooled for each of the Native or fusion proteins, diluted with an equal volume of P6 buffer (25 mM Tris, pH 7.5/1 mM β-glycerol phosphate/0.15 mM NaCl/0.025% sodium azide), and desalted over a BioGel P6 column (BioRad) pre-equilibrated with P6 buffer. Fractions containing GUS activity were pooled, and the finally purified active protein was stored at −80° C.

EXAMPLE 2

Stability in the Blood

Figure 3:
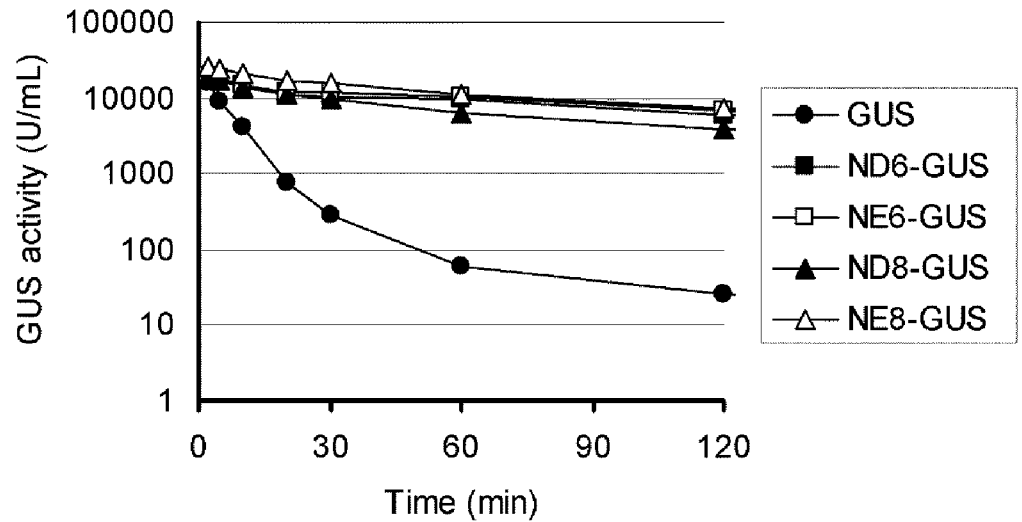
FIG. 3: is a graph showing the time profiles of the blood activity levels of native GUS and GUS fusion protein after they are intravascularly administered in an equivalent amount.
Figure 3:
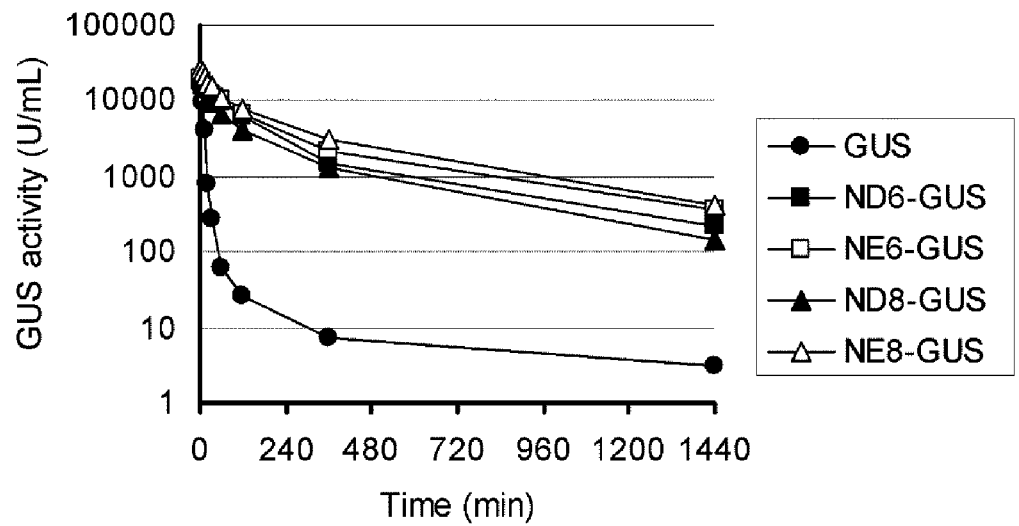

Per 1 g of body weight, 1,000 U of native GUS or one of the NBT-GUSs, both purified, were administered to male, 4-month old C57BL mice (3 animals/group) in the tail vein. Samples of venous blood were collected at 2 min, 5 min, 10 min, 20 min, 30 min, 1 hr, 2 hr, 6 hr, 24 hr after the administration, and GUS activity in the serum was measured. The results are shown in FIG. 3. Comparison between the NBT-GUSs-administered groups and the native GUS-administered group reveals that, at 2 min after the administration, the enzyme activity in the blood was 2-fold higher in the NBT-GUSs-administered groups as compared with the native GUS-administered group. While the enzyme activity in the blood at 30 min after the administration was almost disappeared in the native GUS-administered group, the NBT-GUSs-administered groups retained activity levels, which were even higher than the activity level found at 2 min in the native GUS-administered group. Afterwards, the NBT-GUSs-administered groups continued to show remarkably slower reduction in the enzyme activity levels in the blood as compared with those found in the native GUS-administered group. Even 24 hr (1440 min) after the administration, the residual enzyme activity was detectable in the NBT-GUSs-administered group. A half-life time of the enzyme activity in blood in the native GUS-administered group was 4.9 min, while a half-life time in blood in the NBT-GUS-administered group was prolonged 5-6 times. The results demonstrate that the stability of GUS in the body is remarkably increased by attaching a short peptide of acidic amino acids to the N-terminus of native GUS.

EXAMPLE 3

Effects of GUS on Brain Tissue

Figure 4:
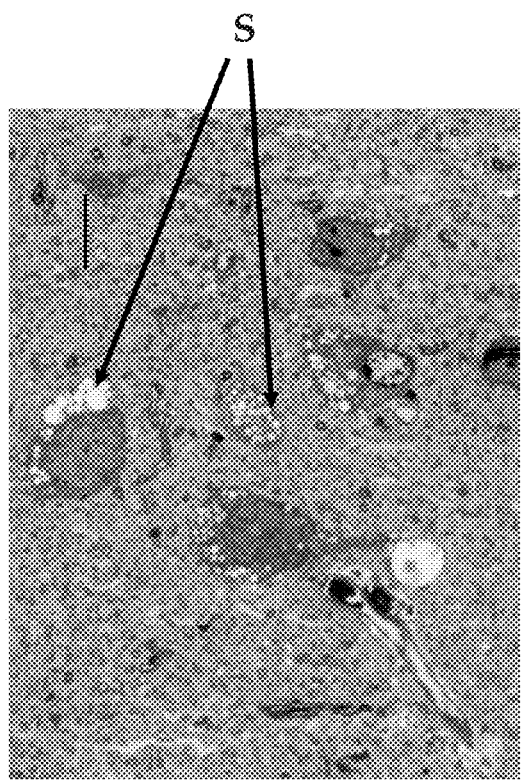
FIG. 4: shows light microscopy of neocortex from native GUS and $D_6$-GUS treated mice. The cortical neuron, hippocampus, and glia cell sections show a reduction of storage (S) in $D_6$-GUS treated compared to GUS treated MPS VII mice.
Figure 4:
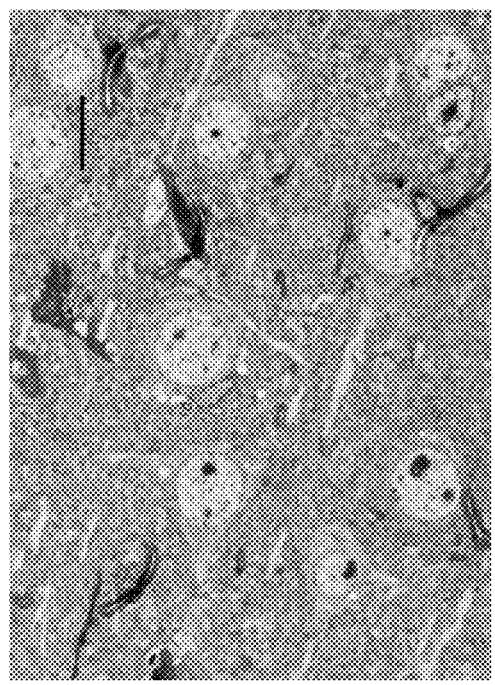

To compare the effectiveness of AAA-tagged and untagged GUS at clearing storage from affected tissues in the MPS VII mouse, the inventors used a protocol in which enzyme was given in 12 weekly treatments with 1 mg/kg enzyme. There were notable differences in which the D6-GUS appeared to be more effective in clearing the storage material. The parietal neocortical neurons and glia had less storage in the D6-GUS-treated MPS VII mice. In brain, the AAA-tagged enzyme showed improved clearance of storage from parietal neocortical neurons and glial cells, where as storage showed minimal or no clearance response to untagged enzyme at the same dose. FIG. 4 shows light microscopy of tissues from native GUS and D6-GUS treated MPS VII mice. The cortical neuron, hippocampus, and glia cell sections show a reduction of storage (S) in $D_6$-GUS treated compared to GUS treated mice.

In these studies, MPS VII/E540A'$^g$ mice were used.[22] These mice carry a GUS transgene that encodes an inactive enzyme, which confers immunotolerance to the human protein. To define the clearance from the blood circulation, 1,000 units per g of body weight of D6-GUS, D8-GUS or untagged GUS were administered to 4-month-old MPS VII mice (3 animals/group) via the tail vein. Samples of venous blood were collected at 2 min, 5 min, 10 min, 20 min, 30 min, 1 h, 2 h, 6 h, and 24 h after administration, and GUS activity in the serum was measured.

To determine the effectiveness of D6-GUS, D8-GUS, and untagged enzyme at reversing storage pathology, three adult animals in each group received twelve weekly doses (5,000 units/g) of D6-GUS, D8-GUS, untagged enzyme or PBS by injection in the lateral tail vein. Animals were killed 1 week after the 12th injection, and the organs were removed for histopathology analysis with light or electron microscopy.

For morphological evaluation, liver, spleen, kidney, brain, heart, femur, and bone marrow from 4-5 month old MPS VII mice treated with D6-GUS (n=2), D8-GUS (n=3), and untagged enzyme (n=3), or buffer (n=2) were collected at necropsy, immersion-fixed in 4% paraformaldehyde/2% glutaraldehyde in PBS, postfixed in osmium tetroxide, and embedded in Spurr's resin. For evaluation of lysosomal storage by light microscopy, toluidine blue-stained 0.5-μm-thick sections were examined. One mouse treated by D6-GUS died immediately after the 12th weekly infusion and was not evaluated morphologically. Tissues from the treated and untreated mice were evaluated for reduction in storage without knowledge of their treatment. Two pathologists (CV, BL) independently evaluated the brain for lysosomal storage.

Some individual elements of the inventors' methodology are generally known or described in detail in numerous laboratory protocols, one of which is Molecular Cloning 2nd edition, (1989) Sambrook, J., Fritsch, E. F. and Maniatis, J., Cold Spring Harbor. As such detailed discussion of their composition and methodology is superfluous.

REFERENCES

Applicants make no statement, inferred or direct, regarding the status of the following references as prior art. Applicants reserve the right to challenge the veracity of any statements made in these references, which are incorporated herein by reference.

[1] Wraith, J. E. (2002) Semin. Neonatol. 7, 75-83.

[2] Barton, N. W., Furbish, F. S., Murray, G. J., Garfield, M. & Brady, R. O. (1990) Proc. Natl. Acad. Sci. USA 87, 1913-1916.

[3] Barton, N. W., Brady, R. O., Dambrosia, J. M., Di Bisceglie, A. M., Doppelt, S. H., Hill, S.C., Mankin, H. J., Murray, G. J., Parker, R. I., Argoff, C. E., et al. (1991) N. Engl. J. Med. 324, 1464-1470.

[4] Murray, G. J. (1987) Methods Enzymol. 149, 25-42.

[5] Furbish, F. S., Steer, C. J., Krett, N. L. & Barranger, J. A. (1981) Biochim. Biophys. Acta 673, 425-434.

[6] Stahl, P. D., Rodman, J. S., Miller, M. J. & Schlesinger, P. H. (1978) Proc. Natl. Acad. Sci. USA 75, 1399-1403.

[7] Achord, D. T., Brot, F. E., Bell, C. E. & Sly, W. S. (1978) Cell 15, 269-278.

[8] Barton, N. W., Brady, R. O., Dambrosia, J. M., Di Bisceglie, A. M., Doppelt, S. H., Hill, S. C., Mankin, H. J., Murray, G. J., Parker, R. I. & Argoff, C. E. (1991) N. Engl. J. Med. 324, 464-470.

[9] Barranger, J. A. & O'Rourke, E. (2001) J. Inherit. Metab. Dis. Suppl 2, 89-96.

[10] Japanese Patent No. 2852127

[11] Sly W S, Quinton B A, McAlister W H, and Rimoin D L, J. Pediatr. 82:249-257 (1973)

[12] Achord, D. T., Brot, F. E., Bell, C. E. & Sly, W. S. (1978) Cell 15, 269-278.

[13] U.S. application Ser. No. 11/484,870, filed Jul. 11, 2006

[14] Neufeld E F, Muenzer J. (2001) The Mucopolysaccharidoses. In Scriver, C. R., Beaudet, A., Valle, D., and Sly. W. S. (eds.), The Metabolic and Molecular Bases of Inherited Diseases. 8th edition ed. McGraw-Hill Professional, New York, Vol. III, pp. 3421-3452.

[15] Tomatsu S, Okamura K, Taketani T, Orii K O, Nishioka T, Gutierrez M A, Velez-Castrillon S, Fachel A A, Grubb J H, Cooper A, Thornley M, Wraith E, Barrera L A, Giugliani R, Schwartz I V, Frenking G S, Beck M, Kircher S G, Paschke E, Yamaguchi S, Ullrich K, Isogai K, Suzuki Y, Orii T, Kondo N, Creer M, Noguchi A. (2005). J Inherit Metab Dis. 28:187-202.

[16] Tomatsu S, Gutierrez M A, Ishimaru T, Pena O M, Montano A M, Maeda H, Velez-Castrillon S, Nishioka T, Fachel A A, Cooper A, Thornley M, Wraith E, Barrera L A, Laybauer L S, Giugliani R, Schwartz I V, Frenking G S, Beck M, Kircher S G, Paschke E, Yamaguchi S, Ullrich K, Isogai K, Suzuki Y, Orii T, Noguchi A. (2005). 28:743-57

[17] Vogler, C., Levy, B., Grubb, J. H., Galvin, N., Tan, Y., Kakkis, E., Pavloff, N. & Sly W. S. (2005), Proc Natl Acad Sci USA. 102:14777-14782.

[18] Dunder, U., Kaartinen, V., Valtonen, P., Vaananen, E., Kosma, V. M., Heisterkamp, N., Groffen, J. & Mononen, I. (2000), FASEB J. 14, 361-367.

[19] Roces D P, Lullmann-Rauch R, Peng J, Balducci C, Andersson C, Tollersrud O, Fogh J, Orlacchio A, Beccari T, Saftig P, von Figura K. (2004), 13:1979-1988.

[20] U.S. application Ser. No. 10/864,758, filed Jun. 10, 2004

[21] U.S. application Ser. No. 11/245,424, filed Oct. 7, 2005

[22] Sly, W. S., Vogler, C., Grubb, J. H., Zhou, M., Jiang, J., Zhou, X. Y., Tomatsu, S., Bi, Y. & Snella, E. M. (2001), Proc. Natl. Acad. Sci. USA 98, 2205-2210.

What is claimed is:

1. A method of treating a subject with type VII mucopolysaccharidosis, said method comprising, injecting into the blood, a therapeutic effective amount of physiologically active human β-glucuronidase without the signal sequence, with a short peptide consisting of about 6 aspartic acid residues attached to the N-terminus of the physiologically active human β-glucuronidase, for a period of about 12 weeks, whereby the physiologically active human β-glucuronidase improves the clearance of lysosomal storage material in the brain.

2. The method of claim 1, wherein the short peptide consisting of about 6 aspartic acids is attached to the N-terminus of physiologically active the human β-glucuronidase by a linker peptide.

3. The method of claim 1, wherein the therapeutic effective amount is about 1 milligram per gram body weight.

4. The method of claim 1, wherein the therapeutic effective amount is about 5000 units per gram body weight.

5. The method of claim 1, wherein the therapeutic effective amount of the physiologically active human β-glucuronidase without the signal sequence, with the short peptide consisting of about 6 aspartic acids attached to the N-terminus of the physiologically active human β-glucuronidase is injecting into the blood on a weekly basis.

6. The method of claim 1, wherein the physiologically active human β-glucuronidase comprises the amino acid sequence of SEQ ID NO: 2.

7. he method of claim 1 whereby the subject is an adult.

8. A method of treating a subject with type VII mucopolysaccharidosis the method comprising, injecting into the blood, for a period of about 12 weeks, a therapeutic effective amount of physiologically active human β-glucuronidase without the signal sequence, with a short peptide, attached to the N-terminus of the physiologically active human β-glucuronidase, the amino acid sequence of the short peptide selected from the group consisting of consisting of about 6 aspartic acid residues, about 8 aspartic acid residues, about 6 glutamic acid residues, and about 8 glutamic acid residues, whereby the physiologically active human β-glucuronidase improves the clearance of lysosomal storage material in the brain.

9. The method of claim 8 whereby the amino acid sequence of the physiologically active human β-glucuronidase without the signal sequence, with a short peptide attached at the N-termins is selected from the group consisting of SEQ ID NO: 11, SEQ ID NO: 13, SEQ ID NO: 15, and SEQ ID NO: 17.

10. The method of claim 8, wherein the short peptide is attached to the N-terminus of physiologically active the human β-glucuronidase by a linker peptide.

11. The method of claim 8, wherein the therapeutic effective amount is about 1 milligram per gram body weight.

12. The method of claim 8, wherein the therapeutic effective amount is about 5000 units per gram body weight.

13. The method of claim 8, wherein the therapeutic effective amount of physiologically active human β-glucuronidase without the signal sequence, with a short peptide, attached to the N-terminus of the physiologically active human β-glucuronidase, the amino acid sequence of the short peptide selected from the group consisting of consisting of about 6 aspartic acid residues, about 8 aspartic acid residues, about 6 glutamic acid residues, and about 8 glutamic acid residues, is injecting into the blood on a weekly basis.

14. The method of claim 8, whereby the subject is an adult.

* * * * *